(12) United States Patent
Olivares

(10) Patent No.: US 10,648,103 B2
(45) Date of Patent: May 12, 2020

(54) UNIVERSAL BLOCKING OLIGO SYSTEM AND IMPROVED HYBRIDIZATION CAPTURE METHODS FOR MULTIPLEXED CAPTURE REACTIONS

(71) Applicant: INVITAE CORPORATION, San Francisco, CA (US)

(72) Inventor: Eric Olivares, San Francisco, CA (US)

(73) Assignee: INVITAE CORPORATION, San Francisco, CA (US)

( * ) Notice: Subject to any disclaimer, the term of this patent is extended or adjusted under 35 U.S.C. 154(b) by 234 days.

(21) Appl. No.: 15/514,957

(22) PCT Filed: Oct. 8, 2015

(86) PCT No.: PCT/IB2015/057679
§ 371 (c)(1),
(2) Date: Mar. 28, 2017

(87) PCT Pub. No.: WO2016/055956
PCT Pub. Date: Apr. 14, 2016

(65) Prior Publication Data
US 2017/0218537 A1    Aug. 3, 2017

Related U.S. Application Data

(60) Provisional application No. 62/062,612, filed on Oct. 10, 2014, provisional application No. 62/062,616, filed on Oct. 10, 2014.

(51) Int. Cl.
*C40B 40/08*     (2006.01)
*C12Q 1/6806*    (2018.01)
(Continued)

(52) U.S. Cl.
CPC ............ *C40B 40/08* (2013.01); *C12Q 1/6806* (2013.01); *C12Q 1/6809* (2013.01);
(Continued)

(58) Field of Classification Search
None
See application file for complete search history.

(56) References Cited

U.S. PATENT DOCUMENTS

| 2007/0219367 A1 | 9/2007 | Shchepinov et al. |
| 2014/0031240 A1 | 1/2014 | Behlke et al. |
| 2014/0243232 A1* | 8/2014 | Meredith et al. .... C12Q 1/6832 506/9 |

FOREIGN PATENT DOCUMENTS

WO    WO 2014/008447    7/2013

OTHER PUBLICATIONS

International Preliminary Report on Patentability dated Apr. 20, 2017 for Appln. No. PCT/IB2015/057679.
(Continued)

*Primary Examiner* — Kaijiang Zhang
(74) *Attorney, Agent, or Firm* — Pillsbury Winthrop Shaw Pittman, LLP

(57) ABSTRACT

Provided herein, in some embodiments, are novel compositions and improved methods for nucleic acid manipulation and analysis that can be applied to multiplex nucleic acid sequencing. In certain embodiments, the novel compositions and methods presented herein are more cost effective, more conducive to automation, and faster than traditional approaches. Also provided herein are novel blocking nucleic acids.

19 Claims, 1 Drawing Sheet

(51) Int. Cl.
  *C12Q 1/6809* (2018.01)
  *C12Q 1/6832* (2018.01)
  *C12Q 1/6853* (2018.01)
  *C40B 30/04* (2006.01)
  *C40B 40/06* (2006.01)
  *C40B 70/00* (2006.01)
  *C12Q 1/6858* (2018.01)
  *C12Q 1/686* (2018.01)
  *C12Q 1/6874* (2018.01)
  *C12Q 1/6883* (2018.01)

(52) U.S. Cl.
  CPC ......... *C12Q 1/6832* (2013.01); *C12Q 1/6853* (2013.01); *C40B 30/04* (2013.01); *C40B 40/06* (2013.01); *C40B 70/00* (2013.01); *C12Q 1/686* (2013.01); *C12Q 1/6858* (2013.01); *C12Q 1/6874* (2013.01); *C12Q 1/6883* (2013.01)

(56) References Cited

OTHER PUBLICATIONS

Ausubel et al.; "Current Protocols in Molecular Biology"; vol. 1, 1993, pp. 1-12.
NimbleGen; SeqCap EZ library SR User's Guide, Version 4.1, 2013, pp. 1-60.
Hasen et al.; "A massive parallel sequencing workflow for diagnostic genetic testing of mismatch repair genes", Molecular Genetics & Genomic Medicine; 2014, pp. 186-200.
Brookman-Amissah, N., et al., Increasing On-Target NGS Reads: Use of Adapter Blocking Oligos for In-Solution Hybridization Improves Target Capture Performance, Genetic Engineering & Biotechnology News, vol. 34, No. 6, Mar. 15, 2014; pp. 24-24.
Lupski, J.R., et al., "Exome sequencing revolves apparent incidental findings and reveals further complexity of SH3TC2 variant alleles causing Charcot-Marie-Tooth neuropathology," Genome Medicine, vol. 5, No. 6, Jun. 27, 2013, p. 57.
Rohland, N., et al., "Cost-effective, high-throughput DNA sequencing libraries for multiplexed target capture," Genome Research, vol. 22, No. 5, Jan. 20, 2012, pp. 939-946.
Rohland, N., et al., Cost-effective, high-throughput DNA sequencing libraries for multiplexed target capture, Genome, vol. 22, No. 5, Jan. 20, 2012, pp. 1-29.
Extended European Search Report dated Feb. 18, 2016, for European Patent Application No. 15849044.1.
International Search Report dated Feb. 2, 2016 for Appln. No. PCT/IB2015/057679.
Hansen et al., "A massive parallel sequencing workflow for diagnostic genetic testing of mismatch repair genes", Molecular Genetics & Genomic Medicine, Jan. 21, 2014, vol. 2, Issue 2, pp. 186-200.

* cited by examiner

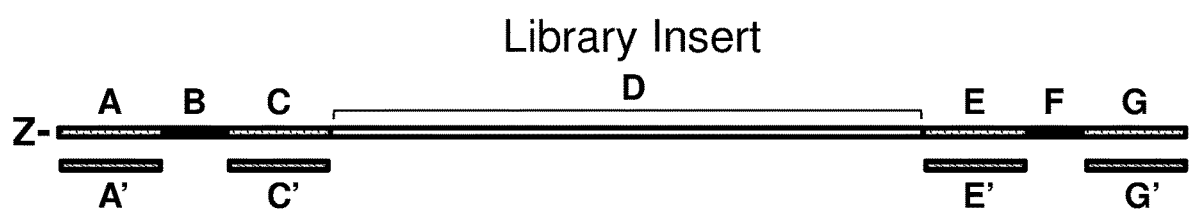

UNIVERSAL BLOCKING OLIGO SYSTEM AND IMPROVED HYBRIDIZATION CAPTURE METHODS FOR MULTIPLEXED CAPTURE REACTIONS

RELATED PATENT APPLICATION

This application is a U.S. National Stage filing of International Patent Application No. PCT/IB2015/057679, filed Oct. 8, 2015, entitled "UNIVERSAL BLOCKING OLIGO SYSTEM AND IMPROVED HYBRIDIZATION CAPTURE METHODS FOR MULTIPLEXED CAPTURE REACTIONS", which claims the benefit of U.S. Provisional Patent Application No. 62/062,612 filed on Oct. 10, 2014, entitled "UNIVERSAL BLOCKING OLIGO SYSTEM FOR MULTIPLEXED CAPTURE REACTIONS", naming Eric Olivares as an inventor, and U.S. Provisional Patent Application No. 62/062,616 filed on Oct. 10, 2014, entitled "METHODS OF HYBRIDIZATION CAPTURE USING NUCLEIC ACID BAITS FROM PAIRED-END SEQUENCING", naming Eric Olivares as an inventor. The entire content of the foregoing patent applications are incorporated herein by reference, including all text, tables and drawings.

FIELD

The technology relates in part to compositions and methods of nucleic acid manipulation, analysis and high-throughput sequencing.

BACKGROUND

Genetic information of living organisms (e.g., animals, plants, microorganisms, viruses) is encoded in deoxyribonucleic acid (DNA) or ribonucleic acid (RNA). Genetic information is a succession of nucleotides or modified nucleotides representing the primary structure of nucleic acids. The nucleic acid content (e.g., DNA) of an organism is often referred to as a genome. In humans, the complete genome typically contains about 30,000 genes located on twenty-four (24) chromosomes. Most gene encodes a specific protein, which after expression via transcription and translation fulfills a specific biochemical function within a living cell.

Many medical conditions are caused by one or more genetic variations within a genome. Some genetic variations may predispose an individual to, or cause, any of a number of diseases such as, diabetes, arteriosclerosis, obesity, various autoimmune diseases and cancer (e.g., colorectal, breast, ovarian, lung), for example. Such genetic diseases can result from an addition, substitution, insertion or deletion of one or more nucleotides within a genome.

Genetic variations can be identified by multiplex analysis of mixtures of nucleic acids often obtained from multiple sources, for example by use of next generation sequencing techniques. Such multiplex analysis often involves a significant amount of manipulation of nucleic acids prior to analysis involving many different steps that are not conducive to high-throughput processing. In addition, current methods of nucleic acid manipulation are often costly, time consuming and often present substantial pitfalls that can lead to contamination of samples. Compositions and methods herein offer significant improvements over current nucleic acid manipulation and analysis techniques that are more conducive to high-throughput automation, more cost efficient, less time consuming and/or provide for less risk of contamination.

SUMMARY

Presented herein, in some aspects, is a composition for use in massive parallel nucleic acid sequencing comprising, a) a library of nucleic acids comprising a plurality of library inserts where each nucleic acid of the library comprises (i) at least one library insert obtained from one of four or more samples, (ii) a first non-native nucleic acid, and (iii) a second non-native nucleic acid, where the first non-native nucleic acid and the second non-native nucleic acid are located on opposing sides of the at least one library insert, and the first non-native nucleic acid comprises a first distinguishable nucleic acid barcode and the second non-native nucleic acid comprises a second distinguishable nucleic acid bar code, where the first and second distinguishable nucleic acid barcodes are unique to the one of the four or more samples; and b) four U-block nucleic acids, where (i) a first and second U-block nucleic acid are configured to hybridize to the first non-native nucleic acid on opposing sides of the first distinguishable nucleic acid barcode and (ii) a third and fourth U-block nucleic acid are configured to hybridize to the second non-native nucleic acid on opposing sides of the second distinguishable nucleic acid barcode, and (iii) each of the U-block nucleic acids do not substantially hybridize to a portion of the first or second distinguishable nucleic acid barcodes. In certain aspects, the library of nucleic acids comprises at least eight distinguishable nucleic acid barcodes.

In some aspects the compositions further comprise one or more capture nucleic acids, where (i) the capture nucleic acids comprise a member of a binding pair, and (ii) each of the capture nucleic acids is configured to specifically hybridize to a subset of the one or more library inserts.

Also presented herein, in certain embodiments, is method of analyzing a nucleic acid library comprising, a) obtaining a library of nucleic acids comprising a plurality of library inserts where each nucleic acid of the library comprises (i) at least one library insert obtained from one of four or more samples, (ii) a first non-native nucleic acid, and (iii) a second non-native nucleic acid, where the first non-native nucleic acid and the second non-native nucleic acid are located on opposing sides of the at least one library insert, and the first non-native nucleic acid comprises a first distinguishable nucleic acid barcode and the second non-native nucleic acid comprises a second distinguishable nucleic acid bar code, where the first and second distinguishable nucleic acid barcodes are unique to the one of the four or more samples; b) contacting the library of nucleic acids with four U-block nucleic acids, where (i) a first and second U-block nucleic acid are configured to hybridize to the first non-native nucleic acid on opposing sides of the first distinguishable nucleic acid barcode and (ii) a third and fourth U-block nucleic acid are configured to hybridize to the second non-native nucleic acid on opposing sides of the second distinguishable nucleic acid barcode, and (iii) each of the U-block nucleic acids does not substantially hybridize to a portion of the first or second distinguishable nucleic acid barcodes; and c) contacting the library of nucleic acids with one or more capture nucleic acids, each comprising a first member of a binding pair, where the one or more capture nucleic acids are configured to specifically hybridize to a subset of the nucleic acids of the library; d) capturing the capture nucleic acids, thereby providing captured nucleic acids comprising the subset of nucleic acids of the library; e) contacting the captured nucleic acids with a set of primers under amplification condition, thereby providing amplicons; and f) analyzing the amplicons.

In certain aspects the analyzing comprising providing sequence reads. In some aspects sequencing reads can be obtained by a method comprising massive parallel sequencing and/or pair-end sequencing.

In certain aspects regarding the compositions and methods herein, the non-native nucleic acids comprise universal nucleic acids. In some aspects the nucleic acids of the library comprise four or more, or ten or more barcode nucleic acids. In some aspects each library insert comprises one or two barcode sequences. In certain aspects U-block nucleic acids comprise a length of 10 to 40 nucleotides. In certain aspects U-block nucleic acids comprise a length of 10 to 20 nucleotides. In some aspects the U-block nucleic acids comprise locked nucleic acids and/or bridged nucleic acids. In certain aspects the U-block nucleic acids comprise a melting temperature of between about 65° C. and about 90° C. In certain aspects the U-block nucleic acids comprise a melting temperature of at least 65° C. or at least 75° C. In some aspects the U-block nucleic acids do not comprise a degenerate nucleotide base. In some aspects the U-block nucleic acids do not comprise a 3-nitropyrrole, a 5-nitroindole, inosine, a 2'-deoxyinosine, analogues, derivatives or combinations thereof.

In some aspects provided herein is a method of analyzing a nucleic acid library comprising, a) obtaining a library of nucleic acids comprising a first set of amplicons, where each amplicon comprises a first non-native nucleic acid and a second non-native nucleic acid, one or more distinguishable identifiers, and a library insert obtained from one of one or more samples, where the library insert is located between the first and the second non-native nucleic acids, b) preparing a mixture comprising contacting the nucleic acids of the library with one or more blocking nucleic acids and capture nucleic acids, where (i) the one or more blocking nucleic acids are configured to specifically hybridize to the first and second non-native nucleic acids, (ii) the capture nucleic acids comprise a first member of a binding pair, and (ii) the capture nucleic acids are configured to specifically hybridize to a subset of amplicons of the first set, c) purifying the mixture, thereby providing purified nucleic acid, where the purified nucleic acid comprises the nucleic acids of the library, the one or more blocking nucleic acids, and the capture nucleic acids, d) hybridizing the purified nucleic acid under hybridization conditions, e) capturing the capture nucleic acids, thereby providing captured nucleic acid, f) contacting the captured nucleic acid with a set of primers under amplification condition, thereby providing a second set of amplicons, and g) analyzing the second set of amplicons. In some aspects, the amplification conditions comprise a heat-stable polymerase and/or a polymerase chain reaction. In certain aspects the preparing in (b) comprises contacting the nucleic acids of the library with competitor nucleic acids. In some embodiments, the capture nucleic acids are configured to specifically hybridize to a portion of the library insert. In certain embodiments the one or more blocking nucleic acids are configured to specifically hybridize to a portion of the first non-native nucleic acid and/or the second non-native nucleic acid. In certain embodiments the one or more blocking nucleic acids comprise locked nucleic acids and/or bridged nucleic acids.

In some aspects the capture nucleic acids comprising a first member of a binding pair are configured to specifically hybridize to a portion of an exon, an intron, a portion of a selected chromosome and/or to a regions of DNA comprising a genetic variation (e.g., a repeat, a polymorphism). In some embodiments the first member of the binding pair comprises a biotin, an antigen, a hapten, an antibody or a portion thereof. In some aspects the capturing in (e) comprises contacting the mixture with a second member of a binding pair. In some aspects the second member of the binding pair comprises avidin, protein A, protein G, an antibody, or a binding portion thereof. In certain embodiments the second member of the binding pair comprises a substrate. In some embodiments, the substrate comprises a magnetic compound. In some embodiments, the substrate comprises a bead. In some embodiments, the substrate comprises polystyrene, polycarbonate, sepharose or agarose. In some embodiments, the substrate comprises a metal.

In certain embodiments the hybridization conditions comprise denaturing. In certain embodiments the hybridization conditions comprise hybridizing the captured nucleic acids to a portion of one or more of the amplicons of the first set. In certain embodiments the hybridization conditions comprise incubating the captured nucleic acid at a temperature between about 25° C. and about 70° C. In certain embodiments the hybridization conditions comprise incubating the captured nucleic acid at a temperature between about 35° C. and about 60° C. In certain embodiments the hybridization conditions comprise incubating for an amount of time between about 1 hour and about 24 hours or between about 12 hours and about 20 hours. In certain embodiments the hybridization conditions do not include a polymerase. In some embodiments the hybridizing in (d) comprises contacting the mixture with a hybridization buffer. In some embodiments the hybridizing in (d) comprises the sequential steps of (i) contacting the mixture with a hybridization buffer, (ii) denaturing and (iii) hybridizing.

In some aspects the analyzing comprises providing sequence reads. Sometimes the sequence reads are obtained by a method comprising next generation sequencing (e.g., massive parallel sequencing). Sometime the sequence reads are obtained by a method comprising pair-end sequencing.

In certain embodiments the first non-native nucleic acid comprises at least one nucleic acid barcode. In certain embodiments the second non-native nucleic acid comprises at least one nucleic acid barcode.

In certain embodiments the claimed methods herein do not comprise a drying step. In some embodiments the method does not comprise a denaturation step prior to (c). In some embodiments the method does not comprise a denaturation step prior to (d). In certain embodiments the method does not comprise heating to a temperature above 80° C. prior to (d). In certain embodiments the method does not comprise heating to a temperature above 90° C. prior to (d). In some embodiments, the mixture is not immobilized on a substrate of a flow cell or an array prior to (e). In some embodiments the purifying in (c) does not comprise addition of a second member of a binding pair configured to bind to the first member of the binding pair.

In some aspects samples can be obtained from one or more species, one or more tissues, one or more mammals or one or more human subjects.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1 shows an embodiment of a blocking method comprising four U-block nucleic acids (A', C', E' and G')). FIG. 1 shows a representative nucleic acid of a library (Z) comprising a library insert (D) and distinguishable nucleic acid barcodes (B and F), where a plurality of different inserts and different distinguishable barcodes are present in the many nucleic acids of the library. FIG. 1 shows U-block nucleic acids (A', C', E' and G')) each of which are configured to specifically hybridize to portions of non-native nucleic acids (A, C, E and G) as shown, and which U-block nucleic acids hybridize adjacent to nucleic acid barcodes (B or F).

DETAILED DESCRIPTION

Next generation sequencing (NGS) allows for sequencing and analysis of nucleic acids on a genome-wide scale by methods that are faster and cheaper than traditional methods of sequencing. Methods and compositions herein provide for improvements of advanced sequencing technologies that can be used to locate and identify genetic variations and/or associated diseases and disorders. In some embodiments, provided herein are methods that comprise, in part, manipulation and preparation of nucleic acid mixtures for NGS.

Sequencing applications with genomic nucleic acids as the target material often requires selection of nucleic acid targets of interest from a highly complex mixture. The quality of the sequencing efforts often depend on the efficiency of the selection process, which, in turn, relies upon how well nucleic acid targets can be enriched relative to non-target sequences. Selection and enrichment of a nucleic acid library sometimes comprises capture of adapter-ligated inserts (e.g., genomic DNA inserts) by a hybrid capture approach.

Most next generation sequencing library molecules contain non-native sequences (e.g., adapter nucleic acid, barcode sequences, primer binding sites, and universal sequences) which enable their subsequent sequencing. During hybridization capture reactions, non-native sequences can anneal to one another resulting in contamination of an enriched nucleic acid pool. A large fraction of these unwanted sequences are often due to undesired hybridization events between portions of terminal adapter sequences that are ligated to library inserts. Sometimes multiple library inserts can non-specifically anneal to each other through their terminal adapters, thereby resulting in a "daisy chain" of otherwise unwanted DNA fragments being linked and isolated together.

One method of reducing the so called "daisy chain" effect utilizes blocking nucleic acids directed to hybridize to large portions of adapter sequences. For traditional approaches, a blocking nucleic acid is required for each side of an adapter and each blocking nucleic acid contains a perfect complementary match to the adapter sequences (including the barcode sequences (e.g., index sequences)) contained in each of the adapters. For high throughput multiplex sequencing methods, multiple libraries are often mixed, each library consisting of different adapters sequences and different barcode sequences. For such multiplex approaches, multiple sets of traditional blocking nucleic acids are required to be synthesized, each specific for the adapters of each library. This approach is cumbersome and costly and requires manufacture of many different, relatively long oligonucleotides which hinders efficient and cost-effective automation of a library preparation and sequencing process.

Provided herein, in some aspects, are novel and improved compositions for, and methods of, reducing unwanted capture events. In some embodiments, presented herein are novel U-block (i.e., universal blocking) nucleic acids. The compositions comprising the novel U-block nucleic acid presented herein and methods that utilize the U-block nucleic acids provided herein are less costly than traditional approaches, increase efficiency and work flow, and are more favorable to automation.

Further, traditional applications of a hybrid capture approach often involve combining a pool of adapter-ligated library inserts or amplicons thereof with C0t-1 DNA and blocking oligonucleotides followed by a drying step. The drying step is often conducted in a vacuum which is time consuming and is performed in an open system which provides for high risk of cross-contamination between samples. After drying, samples are denatured followed by annealing for several days. Biotinylated capture oligonucleotides (e.g., "baits") are then added and the hybridized nucleic acids are typically pulled down with avidin coated beads. The retained pool of nucleic acids are then eluted from the beads and can be introduced into an automated sequencing process. The above described procedure is inefficient and time consuming, is not conducive to automation and can lead to cross-contamination.

Presented herein, in some aspects, are improved method for manipulating and preparing a nucleic acid library for analysis (e.g., for high throughput sequencing) which methods do not require prolonged incubation times and/or a drying step.

Subjects

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. A subject can be a patient (e.g. a human patient).

Samples

Provided herein are methods and compositions for analyzing a sample. A sample (e.g., a sample comprising nucleic acid) can be obtained from a suitable subject. A sample can be isolated or obtained directly from a subject or part thereof. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid).

In some embodiments, a sample comprises nucleic acid, or fragments thereof. A sample can comprise nucleic acids obtained from one or more a subjects. In some embodiments a sample comprises nucleic acid obtained from a single subject. In some embodiments, a sample comprises a mixture of nucleic acids. A mixture of nucleic acids can comprise two or more nucleic acid species having different nucleotide sequences, different fragment lengths, different origins (e.g., genomic origins, cell or tissue origins, subject origins, the like or combinations thereof), or combinations thereof. A sample may comprise synthetic nucleic acid.

Nucleic Acids

The terms "nucleic acid" refers to one or more nucleic acids (e.g., a set or subset of nucleic acids) of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. Unless specifically limited, the term encompasses nucleic acids comprising deoxyribonucleotides, ribonucleotides and known analogs of natural nucleotides. A nucleic acid may include, as equivalents, derivatives, or variants thereof, suitable analogs of RNA or DNA synthesized from nucleotide analogs, single-stranded ("sense" or "antisense", "plus" strand or "minus" strand, "forward" reading frame or "reverse" reading frame) and double-stranded polynucleotides. Nucleic acids may be single or double stranded. A nucleic acid can be of any length of 2 or more, 3 or more, 4 or more or 5 or more contiguous nucleotides. A nucleic acid can comprise a specific 5' to 3' order of nucleotides known in the art as a sequence (e.g., a nucleic acid sequence).

A nucleic acid may be naturally occurring and/or may be synthesized, copied or altered by the hand of man. For, example, a nucleic acid may be an amplicon. A nucleic acid may be from a nucleic acid library, such as a gDNA, cDNA or RNA library, for example. A nucleic acid can be synthesized (e.g., chemically synthesized) or generated (e.g., by polymerase extension in vitro, e.g., by amplification, e.g., by PCR). A nucleic acid may be, or may be from, a plasmid, phage, virus, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. Nucleic acids (e.g., a library of nucleic acids) may comprise nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples). Nucleic acid provided for processes or methods described herein may comprise nucleic acids from 1 to 1000, 1 to 500, 1 to 200, 1 to 100, 1 to 50, 1 to 20 or 1 to 10 samples.

The term "gene" means the segment of DNA involved in producing a polypeptide chain and can include regions preceding and following the coding region (leader and trailer) involved in the transcription/translation of the gene product and the regulation of the transcription/translation, as well as intervening sequences (introns) between individual coding segments (exons). A gene may not necessarily produce a peptide or may produce a truncated or non-functional protein due to genetic variation in a gene sequence (e.g., mutations in coding and non-coding portions of a gene). A gene, whether functional or non-functional, can often be identified by homology to a gene in a reference genome.

Oligonucleotides are relatively short nucleic acids. Oligonucleotides can be from about 2 to 150, 2 to 100, 2 to 50, or 2 to about 35 nucleic acids in length. In some embodiments oligonucleotides are single stranded. In certain embodiments, oligonucleotides are primers. Primers are often configured to hybridize to a selected complementary nucleic acid and are configured to be extended by a polymerase after hybridizing.

Nucleic Acid Isolation and Purification

Nucleic acid may be derived, isolated, extracted, purified or partially purified from one or more subjects, one or more samples or one or more sources using suitable methods known in the art. Any suitable method can be used for isolating, extracting and/or purifying nucleic acid.

The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate, salts, buffers, detergents, and the like, or combinations thereof) than the amount of non-nucleic acid components present prior to subjecting the nucleic acid to a purification procedure. A composition comprising purified nucleic acid may be at least about 60%, 70%, 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. A composition comprising purified nucleic acid may comprise at least 80%, 81%, 82%, 83%, 84%, 85%, 86%, 87%, 88%, 89%, 90%, 91%, 92%, 93%, 94%, 95%, 96%, 97%, 98%, 99% or greater than 99% of the total nucleic acid present in a sample prior to application of a purification method.

In some embodiments purifying a mixture (e.g., purifying nucleic acids in a mixture) provides purified nucleic acid. In certain embodiments, a mixture comprising nucleic acids of a library, blocking nucleic acids, capture nucleic acids, competitor nucleic acids and/or combinations thereof, is purified, thereby providing purified nucleic acid. Nucleic acid purification sometimes comprises a DNA clean-up column or DNA clean up beads. Various nucleic acid clean-up columns, resins, substrates and kits are known in the art. Any suitable nucleic acid purification methods, resin, bead, substrate or kit can be used with a method herein. For example, a nucleic acid purification method can comprise binding (e.g., non-covalently binding) nucleic acids to a suitable cation exchange resin (e.g., a cationic bead) comprising a metal, pull-down of the bound nucleic acid complexes by use of a magnet followed by elution of bound nucleic acids by addition of a low salt buffer. For example, in certain embodiments, a nucleic acid purification comprises use of AMPureXP magnetic beads (Beckman Coulter, Inc., Indianapolis Ind., (USA)) or the like. Methods of nucleic acid purification utilized herein are often modified for optimal recovery of short nucleic acids (e.g., blocking nucleic acids) as well as library inserts (e.g., adapter-ligated inserts and amplicons thereof). In certain embodiments nucleic acid purification methods herein are modified for optimal recovery of nucleic acids with an average or absolute length of about 5 to about 1000 nucleotides, 5 to about 800 nucleotides, or 5 to about 500 nucleotides. In certain embodiments a method of nucleic acid purification used herein employs a ratio of nucleic acid binding resin (e.g. nucleic acid binding beads, nucleic acid binding substrate, e.g., a 100% slurry) to a nucleic acid containing mixture is 1.8:1, 1.9:1, 2:1, 2.1:1, 2.2:1, 2.3:1, 2.4:1, 2.5:1, 2.6:1, 2.7:1, 2.8:1, 2.9:1 or 3:1 (vol:vol).

In some embodiments a purification process comprises a wash step. In some embodiments a purification process comprises an elution step.

In some embodiments a purification process as described herein does not comprise a drying step, the use of a vacuum (e.g., a speed vac) and/or lyophilization. Such methods result in a high risk of cross-contamination. In some embodiments, although the capture nucleic acids of the mixture often comprise a member of a binding pair, a purification process as described herein does not comprise the use of a second member of a binding pair. In some embodiments, a purification method is conducted in the absence of a hybridization buffer. In some embodiments, a purification method is conducted in the absence of added calcium or magnesium salts. In some embodiments, a purification method is conducted in the absence of a detergent (e.g., SDS), Ficoll, BSA, and/or polyvinylpyrrolidone.

Hybridization

Substantially complementary single stranded nucleic acids can hybridize to each other under hybridization conditions, thereby forming a nucleic acid that is partially or fully double stranded. All or a portion of an nucleic acid sequence may be substantially complementary to another nucleic acid sequence, in some embodiments. As referred to herein, "substantially complementary" refers to nucleotide sequences that can hybridize with each other under suitable hybridization conditions. Hybridization conditions can be altered to tolerate varying amounts of sequence mismatch within complementary nucleic acids that are substantially complementary. Substantially complementary portions of nucleic acids that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In some embodiments substantially complementary portions of nucleic acids that can hybridize to each other are 100% complementary. Nucleic acids, or portions thereof, that are configured to hybridize to each other often comprise nucleic acid sequences that are substantially complementary to each other.

As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acid. For example, specific hybridization includes the hybridization of a capture nucleic acid to a portion of a target amplicon that is substantially complementary to the capture nucleic acid. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more.

In some embodiments methods described herein comprise hybridizing nucleic acids under hybridization conditions. Conditions that favor hybridization of substantially complementary nucleic acids are referred to herein as hybridization conditions. Method of altering stringency of hybridization conditions are well known in the art.

Hybridization conditions can be determined and/or adjusted, depending on the characteristics of nucleic acids used in an assay. Methods for optimizing hybridization conditions are known in the art, and may be found in Current Protocols in Molecular Biology, John Wiley & Sons, N.Y., 6.3.1-6.3.6 (1989). Nucleic acid sequence content (e.g., GC content, degree of mismatch) and/or length sometimes may affect hybridization of substantially complementary nucleic acids. Hybridization conditions often comprise parameters that can be adjusted for optimal annealing of two or more substantially complementary nucleic acids of interest. Non-limiting examples of such adjustable parameters include temperature, monovalent or divalent ion and/or cation concentration, (e.g., Mg concentration), buffer concentration, phosphate concentration, glycerol concentration, DMSO concentration, nucleic acid concentration, the like or combinations thereof. Depending on the degree of mismatch between substantially complementary nucleic acids, hybridization conditions can be adjusted to effect the annealing and/or to select for specific hybridization of selected nucleic acids (e.g., oligonucleotides or primers that have a known or predicted melting temperature).

Hybridization conditions often comprise heating or cooling a sample comprising nucleic acid to a suitable temperature. Suitable temperatures for hybridization are sometimes between about 0° C. and 80° C., about 25° C. and 80° C., about 25° C. and 70° C., about 30° C. and 70° C., about 35° C. and 70° C., about 40° C. and 70° C., about 35° C. and 65° C., about 35° C. and 60° C., about 35° C. and 55° C., or about 40° C. and 50° C. In some embodiments hybridization conditions comprise cooling a sample to a temperature of about 40° C., 41° C., 42° C., 43° C., 44° C., 45° C., 46° C., 47° C., 48° C., 49° C., 50° C., 51° C., 52° C., 53° C., 54°

C., or about 55° C. In some embodiments, hybridizing a purified nucleic acid mixture under hybridization conditions comprises a denaturing step followed by a hybridization step (e.g., incubating for a time and temperature suitable for hybridization). Hybridization conditions sometimes comprise denaturing a mixture of nucleic acids immediately followed by cooling of the mixture (e.g., the temperature is quickly ramped) to a suitable hybridization temperature.

In certain embodiment hybridization conditions comprise a denaturing process. Denaturation often comprising increasing the temperature of a sample comprising nucleic acids (e.g., by heating) to a temperature at or above the melting point of one or more double stranded nucleic acids within a sample. In some embodiments denaturation comprises increasing the temperature of a sample from about 70° C. to about 120° C., about 85° C. to about 105° C., about 90° C. to about 105° C. or about 95° C. to about 105° C. In some embodiments denaturation comprises increasing the temperature of a sample to about 70° C. or higher, about 75° C. or higher, about 80° C. or higher, about 85° C. or higher, or to about 90° C., about 91° C., about 92° C., about 93° C., about 94° C., about 95° C., about 96° C., about 97° C., about 98° C., about 99° C., about 100° C., about 101° C., about 102° C., about 103° C., about 104° C. or to about 105° C. In some embodiments nucleic acids are denatured at a desired denaturation temperature for about 1 second to about 30 minutes or longer, about 15 seconds to about 30 minutes, about 30 seconds to about 30 minutes, about 1 minute to about 30 minutes, about 1 minute to about 20 minutes, about 1 minute to about 15 minutes, or about 5 minutes to about 10 minutes.

Hybridization conditions often comprise an incubation period where a sample is held at a desired hybridization temperature for an amount of time. Traditional method of hybridizing nucleic acids of a library, blocking and/or capture nucleic acids require hybridization times in excess of 48 hours. Although any suitable condition can be used for hybridization, certain methods provided herein provide for significantly reduced hybridization times. In certain embodiments hybridization conditions comprise incubating a mixture at a desired hybridization temperature for about 1 minute to about 24 hours, about 5 minutes to about 24 hours, about 10 minutes to about 24 hours, about 15 minutes to about 24 hours, about 30 minutes to about 24 hours, about 1 hour to about 24 hours, about 2 hours to about 24 hours, about 8 hours to about 24 hours, about 10 hours to about 24 hours, about 10 hours to about 20 hours, or about 12 hour to about 20 hours. In some embodiments hybridization conditions comprise incubating a mixture at a desired hybridization temperature for about 10, 11, 12, 13, 14, 15, 16, 17, 18, 19, or 20 hours. In some embodiments hybridization conditions comprise incubating a sample at a desired hybridization temperature for no longer than about 48 hours, no long than about 24 hour or no longer than about 18 hours.

In some embodiments hybridizing comprises contacting nucleic acids with a hybridization buffer. In some embodiments hybridization conditions comprise a mixture of nucleic acids and a suitable hybridization buffer. Hybridization buffers are known in the art and are commercially available. Hybridization buffers can comprise a detergent (e.g., SDS), Ficoll, glycerol, BSA, polyvinylpyrrolidone, dextran glycerol, divalent cations (e.g., calcium and/or magnesium), monovalent cations, phosphate, the like or combinations thereof.

In some embodiments, a method described herein does not comprise a denaturation step prior to a step of hybridizing purified nucleic acid under hybridization conditions.

In certain embodiments, hybridization conditions do not comprise a polymerase. In some embodiments hybridization conditions do not comprise a polymerase chain reaction. In certain embodiments a mixture does not comprise a polymerase until after nucleic acids of a mixture are captured.

Amplification

A nucleic acid can be amplified by a suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof. In some embodiments an amplification reaction comprises a suitable thermal stable polymerase. Thermal stable polymerases a known in the art and are stable for prolonged periods of time, at temperature greater than 80° C. when compared to common polymerases found in most mammals. In certain embodiments the term "amplified" refers to a method that comprises a polymerase chain reaction (PCR). Conditions conducive to amplification (i.e., amplification conditions) are well known and often comprise at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides).

A nucleic acid can be amplified by a thermocycling method or by an isothermal amplification method. In some embodiments a rolling circle amplification method is used. In some embodiments amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge amplification, emulsion PCR, WildFire amplification (e.g., US patent publication US20130012399), the like or combinations thereof.

Nucleic Acid Library

In certain embodiments a nucleic acid library (e.g., a library of nucleic acids) is a collection or subset of the total gDNA, RNA or cDNA obtained from one or more subjects.

A nucleic acid library can comprise single stranded and/or double stranded nucleic acid. A nucleic acid library is often generated from one or more samples and comprises nucleic acids that are endogenous to, or native to, the one or more subjects or organisms from which the samples were obtained. A nucleic acid library often comprises a plurality of nucleic acids or nucleic acid fragments that are endogenous to, or native to, the one or more organisms from which the samples were obtained. Such endogenous or native nucleic acids are sometimes referred to herein as library inserts. Therefore, a plurality of nucleic acids can refer to between $10^3$ and $10^{20}$ nucleic acids. In some embodiments a plurality of nucleic acids refers to $10^3$ or more, $10^4$, or more, $10^5$ or more, $10^6$ or more, $10^7$ or more, $10^8$ or more, $10^9$ or more, $10^{10}$ or more, or $10^{12}$ or more nucleic acids (or inserts). Library inserts can be fragments of genomic DNA (e.g., a genomic DNA library), RNA (e.g., for an RNA library) or cDNA (e.g., a cDNA library). Library inserts can comprise full length genes, cDNA, introns, exons, untranslated regions (e.g., promoters, enhancers, regulatory sequences, and the like) genes, portions thereof or combinations thereof. A library of nucleic acids obtained from any one source or subject often comprises a 1000 or more, 10,000 or more or 100,000 or more library inserts that are different and often distinguishable from each other. In some embodiments a nucleic acid library comprises a plurality of library inserts, where the nucleic acids are prepared, assemble and/or modified for a specific process, non-limiting examples of which include immobilization on a solid phase (e.g., a solid support, e.g., a flow cell, a bead), enrichment, amplification, cloning, detection and/or for nucleic acid sequencing. In some embodiments a library of nucleic acids comprises one or more library inserts obtained from one or more samples (e.g., one or more subjects, one or more tissues, one or more species or a combination thereof). In some embodiments, each nucleic acid of a library comprises at least one library insert (e.g., one, two, three or more inserts), one or more non-native nucleic acids comprising one or more nucleic acid barcodes. In certain embodiments, a nucleic acid library is prepared prior to or during a sequencing process. A nucleic acid library (e.g., a sequencing library) can be prepared by a suitable method as known in the art. A nucleic acid library can be prepared by a targeted or a non-targeted preparation process.

In some embodiments a library of nucleic acids is modified to comprise one or more non-native nucleic acids, often of known composition (e.g., synthetic nucleic acids, heterologous nucleic acids). In some embodiments each nucleic acid of a library comprises 1, 2, 3, 4, 5, 6, 7, 8, 9, or 10 or more non-native nucleic acids. In some embodiments each nucleic acid of a library comprises 1 or 2 non-native nucleic acids. Non-native nucleic acids can be added at a suitable position, for example on one end, the other end, or both ends of a library insert. In some embodiments a nucleic acid of a library comprises a non-native nucleic acid on opposing ends of a library insert. For example, a nucleic acid of a library may comprise a non-native nucleic acid located at the 5' end, and/or 3' end of a library insert. In some embodiments a non-native nucleic acid is covalently bound to a library insert, for example by a suitable phosphodiester bond. In some embodiments a nucleic acid of a library comprises a library insert, a first non-native nucleic acid, and a second non-native nucleic acid, where the first and second non-native nucleic acids are located on opposing sides (e.g., a 5' side and a 3' side) of the library insert.

In certain embodiments non-native nucleic acids are not native to and/or are not endogenous to the one or more subjects or organisms from which a nucleic acid library was obtained. A non-native nucleic acid that is not native and/or not endogenous to a subject or organism from which a nucleic acid library insert was obtained often does not comprise genomic DNA or RNA (e.g., cDNA) that was derived from said subject or organism.

In certain embodiments non-native nucleic acids comprise suitable exogenous nucleic acids and/or suitable synthetic nucleic acids. Non-limiting examples of synthetic nucleic acids include distinguishable identifiers, nucleic acid barcodes (e.g., distinguishable nucleic acid barcodes), capture nucleic acid, sequence tags, random nucleic acid sequences, adapter nucleic acid, a restriction enzyme site, overhangs, a promoter, an enhancer, an origin of replication, a stem loop, a primer binding site, an oligonucleotide annealing site, a suitable integration site (e.g., a transposon, a viral integration site), one or more modified nucleotides, the like, portions thereof or combinations thereof. Non-native nucleic acids can have the same or different nucleic acid sequences. In some embodiments a non-native nucleic acid is configured to hybridize to one or more capture nucleic acids, blocking nucleic acids (e.g., U-block nucleic acids) or primers.

In certain embodiments a nucleic acid library is prepared by a ligation-based library preparation method. In some embodiments non-native nucleic acids are added to a nucleic acid of a library by a ligation-based library preparation method. Ligation-based library preparation methods often make use of one or more adapters. An adapter is often a synthetic nucleic acid (e.g., made by the hand of man) comprising a nucleic acid sequence that is not endogenous to, or present in an organism from which the library is derived. In some embodiments a non-native nucleic acid comprises an adapter. In certain embodiments adapters can be used to prepare library inserts for an analysis (e.g., single-read sequencing, paired-end sequencing and multiplexed sequencing). In some embodiments nucleic acid library preparation comprises ligating one or more adapters to a plurality of library inserts. Adapters can be relatively short double stranded or single stranded oligonucleotides (e.g., from about 2 to about 10, 2 to about 30, 2 to about 50, or 2 to about 100 nucleic acids or more) which can include, for example, distinguishable identifiers, distinguishable nucleic acid barcodes and/or one or more members of a binding pair. An adapter is often located 5' and/or 3' of a library insert. Adapters often flank a library insert. In some embodiments, only one strand of a double stranded adapter is incorporated into a nucleic acid of a library (e.g., ligated to a library insert). Sometimes both strands of a double stranded adapter are incorporated into a library. In some embodiments, a single stranded nucleic acid of a library comprises a 5' adapter and a 3' adapter where the sequence of the 5' and the 3' adapter are substantially different and/or are not substantially complementary.

In certain embodiments, an adapter comprises a portion that is substantially complementary to flow-cell anchors, which portion is sometimes utilized to immobilize a nucleic acid library to a solid support, such as the inside surface of a flow cell, for example. In certain embodiments, an adapter comprises a portion that is substantially complementary to an amplification primer or a sequencing primer, which may be the same, different or overlapping portions of an adapter. In some embodiment, at least one adapter (e.g., a 5' or a 3' adapter) of a nucleic acid of a library comprises a distinguishable identifier (e.g., a distinguishable barcode sequence). In some embodiments both strands of a double stranded adapter comprise a nucleic acid barcode where the nucleic acid barcode of a first strand of the adapter is substantially complementary to the nucleic acid barcode of the second strand of the adapter.

In certain embodiments two or more non-native nucleic acids comprise portions that are substantially identical. Portions of non-native nucleic acids that are substantially identical are sometimes referred to as universal nucleic acids (e.g., universal nucleic acid sequences). In some embodiments non-native nucleic acids comprise one or more universal nucleic acids. In certain embodiments non-native nucleic acid comprises a first universal nucleic acid, a second universal nucleic acid and a nucleic acid barcode where the barcode is located between the first and the second universal nucleic acids. Such non-native nucleic acids can be located 5' and/or 3' of a library insert. For example, in some embodiments a nucleic acid of a library can comprise a first universal nucleic acid, a first nucleic acid barcode and a second universal nucleic acid located 5' of a library insert and a third universal nucleic acid, a second barcode and a fourth universal nucleic acid located 3' of the library insert. In some embodiments, a nucleic acid of a library can comprise a first non-native nucleic acid and a first nucleic acid barcode located 5' of a library insert and a second non-native nucleic acid and a second barcode located 3' of the library insert. In certain embodiments non-native nucleic acids are designed and/or configured to comprise universal sequences that flank a distinguishable barcode. In some embodiments U-block nucleic acids herein are designed and/or configured to specifically hybridize to universal nucleic acid sequences.

In some embodiments a nucleic acid library, or portions thereof, are amplified (e.g., amplified by a PCR-based method). In some embodiments a sequencing method comprises amplification of a nucleic acid library. A nucleic acid library can be amplified prior to or after immobilization on a solid support (e.g., a solid support in a flow cell). In some embodiments a nucleic acid library comprises amplicons. Amplicons of a nucleic acid library can be single stranded or double stranded. In some embodiments amplicons of a nucleic acid library comprise library inserts and adapter sequences (e.g., library inserts flanked by adapter sequences). In some embodiments a nucleic acid library comprises a plurality of amplicons, sometimes referred to herein as a library of amplicons.

In certain embodiments each amplicon of a library of amplicons, comprise a library insert and one or more non-native nucleic acids. For example, in some embodiments an amplicon comprises a library insert and 1, 2, 3, 4, 10 or more, or 50 or more non-native nucleic acids. An amplicon often comprises a library insert located between one or more 5' non-native nucleic acids and one or more 3' non-native nucleic acids. In certain embodiments an amplicon comprises 1, 2, 3, 4, or 5 non-native nucleic acids located 5' of a library insert and 1, 2, 3, 4 or 5 non-native nucleic acids located 3' of a library insert. In some embodiment, an amplicon comprises one or more distinguishable barcodes located 5' of a library insert and one or more distinguishable barcodes located 3' of a library insert. In certain embodiments an amplicon comprises 1, 2, 3, 4, or 5 distinguishable barcodes located 5' of a library insert and 1, 2, 3, 4 or 5 distinguishable barcodes located 3' of a library insert.

In some embodiments an amplicon of a library comprise 1 or more non-native nucleic acids that are substantially identical. Substantially identical nucleic acids are at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical in nucleic acid sequence. Similarly, two or more nucleic acids that are substantially the same refers to two or more nucleic acids that comprise nucleic acid sequences that are substantially identical.

Substantially different nucleic acids refers to two or more nucleic acid sequences that are less than 50%, less than 60%, less than 70%, less than 80%, or less than 85% identical in nucleic acid sequence. Two or more nucleic acids that are substantially different refers to two or more nucleic acids that comprise a nucleic acid sequence that is substantially different.

In some embodiments a method herein comprises obtaining a library of nucleic acids comprising one or more library inserts obtained from one or more samples. In some embodiments a nucleic acid library can be obtained by generating a library as described herein or by a method known in the art. In certain embodiments a nucleic acid library is obtained from a third party, where the third party generated the nucleic acid library. In some embodiments a nucleic acid library is purchased from a vendor. In some embodiments a method herein comprises obtaining a library of nucleic acids comprising one or more library inserts obtained from one or more samples, where each nucleic acid of the library comprises at least one library insert, a first non-native nucleic acid, a second non-native nucleic acid, and one or more nucleic acid barcodes, where the first non-native nucleic acid is located 5' of the at least one library insert and the second non-native nucleic acid is located 3' of the library insert.

Distinguishable Identifiers

In some embodiments a nucleic acid, comprises one or more distinguishable identifiers. A distinguishable identifier can be incorporated into or attached (e.g., covalently, non-covalently, irreversibly or reversibly attached) to a nucleic acid (e.g., a polynucleotide) that allows detection and/or identification of nucleic acids that comprise the identifier. In some embodiments an distinguishable identifier is incorporated into or attached to a nucleic acid before or during a sequencing method (e.g., by a polymerase). Any suitable distinguishable identifier and/or detectable identifier can be used for a composition or method described herein. In certain embodiments a distinguishable identifier can be directly or indirectly associated with (e.g., bound to) a nucleic acid. For example a distinguishable identifier can be covalently or non-covalently bound to a nucleic acid. In some embodiments a distinguishable identifier is bound to or associated with a binding agent or a member of a binding pair that is covalently or non-covalently bound to a nucleic acid. In some embodiments a distinguishable identifier is reversibly associated with a nucleic acid. In certain embodiments a distinguishable identifier that is reversibly associated with a nucleic acid can be removed from a nucleic acid using a suitable method (e.g., by increasing salt concentration, denaturing, washing, adding a suitable solvent and/or by heating).

In some embodiments 1 or more, 2 or more, 3 or more, 4 or more, 5 or more, 6 or more, 7 or more, 8 or more, 9 or more, 10 or more, 20 or more, 30 or more or 50 or more distinguishable identifiers are utilized in a method described herein (e.g., a nucleic acid detection, analysis and/or sequencing method).

In some embodiments a distinguishable identifier is a label. In some embodiments a nucleic acid comprises a detectable label, non-limiting examples of which include a radiolabel (e.g., an isotope), a metallic label, a fluorescent label, a chromophore, a chemiluminescent label, an electrochemiluminescent label (e.g., Origen™), a phosphorescent label, a quencher (e.g., a fluorophore quencher), a fluorescence resonance energy transfer (FRET) pair (e.g., donor and acceptor), a dye, a protein (e.g., an enzyme (e.g., alkaline phosphatase and horseradish peroxidase), an antibody, an antigen or part thereof, a linker, a member of a binding pair, an enzyme substrate, a small molecule (e.g., biotin, avidin), a mass tag, quantum dots, nanoparticles, the like or combinations thereof. Any suitable fluorophore can be used as a label. A light emitting label can be detected and/or quantitated by a variety of suitable techniques such as, for example, flow cytometry, quantitative polymerase chain reaction (qPCR), gel electrophoresis, gene-chip analysis, microarray, mass spectrometry, cytofluorometric analysis, fluorescence microscopy, confocal laser scanning microscopy, laser scanning cytometry, affinity chromatography, manual batch mode separation, electric field suspension, sequencing, the like and combinations thereof.

In some embodiments a distinguishable identifier is a nucleic acid barcode.

Nucleic Acid Barcodes

In some embodiments a non-native nucleic acid comprises one or more distinguishable nucleic acid barcodes (e.g., indexing nucleotides, sequence tags or "barcode" nucleotides). A nucleic acid barcode is often a nucleic acid of a particular sequence that is incorporated within, or appended to (e.g., associated with) a specific nucleic acid, or subset of nucleic acids of a sample to track and/or identify the specific nucleic acid, or subset of nucleic acids, in a mixture of nucleic acids. In certain embodiments a distinguishable nucleic acid barcode comprises a distinguishable sequence of nucleotides usable as an identifier to allow unambiguous identification of one or more nucleic acids (e.g., a subset of nucleic acids) within a sample, method or assay. A distinguishable nucleic acid barcode is often configured to allow unambiguous identification of the origin or identity of a nucleic to which the barcode is associate with. In some embodiments, a distinguishable nucleic acid barcode (e.g., a barcode) can allow identification of the source of a particular nucleic acid in a mixture of nucleic acids obtained from difference sources. In some embodiment, a distinguishable nucleic acid barcode is configured to allow unambiguous identification of the origin or identity of a nucleic acid to which the barcode is associated with. For example, in certain embodiments a distinguishable nucleic acid barcode is specific and/or unique to a certain sample, sample source, a library of nucleic acids obtained from the same subject or tissue, a particular nucleic acid genus or subset, a particular nucleic acid species, nucleic acids from the same chromosome, the like or combinations thereof. In some embodiments nucleic acids comprising inserts derived from a sample, subject or tissue include a nucleic acid barcode that is specific and unique to the sample, subject or tissue thereby allowing unambiguous identification of the nucleic acid and/or insert from a nucleic acid derived from a different sample, subject or tissue. Accordingly, a distinguishable nucleic acid barcode that is unique to a sample, subject or tissue, is often distinguishable from and different from other nucleic acid barcodes in a mixture of nucleic acids. In some embodiments a distinguishable nucleic acid barcode that is unique is different and/or distinguishable from other barcodes in a composition comprising one or more samples derived from one or more sources (e.g., a library of nucleic acid derived from different samples or sources). In some embodiments a distinguishable nucleic acid barcode that is unique to a sample, subject or tissue is associated with (e.g., contained within) nucleic acids derived from the same sample, subject, tissue, or a particular subset thereof. Accordingly, in some embodiments, nucleic acids derived from the same sample, subject, or tissue often comprise at least one distinguishable nucleic acid barcode of identical sequence that is associated with each nucleic acid of the same sample, subject, or tissue.

In some embodiments a distinguishable barcode comprises a distinguishable and/or unique sequence of 4 to 10, 4 to 15, 4 to 20, 4-50 or 20 or more contiguous nucleotides. Two nucleic acid bar codes that are distinguishable may differ in sequence by 1, 2, 3, 4, 5 or more nucleotides. Thus, in certain embodiments, two nucleic acid barcodes that are different and/or distinguishable can be up to 99% identical and comprise a nucleic acid sequence that differs by at least 1 nucleotide. In some embodiments a distinguishable barcode comprises a distinguishable and/or unique sequence of 4, 5, 6, 7, 8, 9, 10, 11, 12, 13, 14 or 15 or more contiguous nucleotides. In some embodiments a distinguishable barcode comprises a distinguishable and/or unique sequence of no more than 10, no more than 15 or no more than 20 contiguous nucleotides. A distinguishable nucleic acid barcode often comprises a first end and a second end. An end of a distinguishable nucleic acid barcode can be identified as the most 5' or most 3' nucleotide base of a distinguishable nucleic acid barcode sequence. For example, in some embodiments, a first end can be identified as the most 5' nucleotide base and the second end can be identified as the most 3' nucleotide base of a distinguishable nucleic acid barcode sequence. A first end and a second end are often located at opposing ends of a distinguishable nucleic acid barcode. In some embodiments any two or more distinguishable nucleic acid barcodes in a library can be distinguished and/or identified by a nucleic acid sequencing method. In some embodiments two or more distinguishable nucleic acid barcodes can be distinguished and/or identified by a hybridization method.

In some embodiments a library of nucleic acids that is obtained from multiple sources or samples comprises multiple distinguishable nucleic acid barcodes. In some embodiments each distinguishable nucleic acid barcode of a library may be used to identify the source of each nucleic acid of a mixed library. For example, a library of nucleic acids obtained from multiple sources may comprise a first library of nucleic acids obtained from a first subject that comprises a first and/or a second distinguishable nucleic acid barcode, a second library of nucleic acids obtained from a second subject that comprise a third and/or a fourth distinguishable nucleic acid barcode, a third library of nucleic acids obtained from a third subject that comprise a fifth and/or a sixth distinguishable nucleic acid barcode, a fourth library of nucleic acids obtained from a fourth subject that comprises a seventh and/or an eighth distinguishable nucleic acid barcode and so forth. In some embodiments each nucleic acid of a library obtained from a single source comprises 1, 2, 3 or 4 distinguishable nucleic acid barcodes, where each distinguishable nucleic acid barcode comprises a different sequence and where each distinguishable nucleic acid barcode redundantly identifies the same source. In some embodiments a nucleic acid library comprising a plurality of library inserts obtained from multiple sample comprises at least 8, at least 10, at least 15, or at least 20 distinguishable nucleic acid barcodes. In some embodiments a nucleic acid library, for example a nucleic acid library comprising a plurality of library inserts obtained from multiple samples or sources, comprises 10 or more, 20 or more, 50 or more or 100 or more distinguishable nucleic acid barcodes.

In some embodiments a non-native nucleic acid comprises one or more distinguishable nucleic acid barcodes. In certain embodiments a non-native nucleic acid comprises 1 or 2 distinguishable nucleic acid barcodes. In certain embodiments a non-native nucleic acid does not comprise a distinguishable nucleic acid barcode. In some embodiments each nucleic acid of the library comprising (i) a library insert, (ii) a first non-native nucleic acid, (iii) a second non-native nucleic acid, and (iv) a distinguishable nucleic acid barcode, where the first non-native nucleic acid and the second non-native nucleic acid are located on opposing sides of the library insert, and the first non-native nucleic acid or the second non-native nucleic acid comprise the distinguishable nucleic acid barcode. In some embodiments each nucleic acid of the library comprising (i) a library insert, (ii) a first non-native nucleic acid, (iii) a second non-native nucleic acid, (iv) a first distinguishable nucleic acid barcode and (v) a second distinguishable nucleic acid barcode, where the first non-native nucleic acid and the second non-native nucleic acid are located on opposing sides of the library insert, the first non-native nucleic acid comprises the first distinguishable nucleic acid barcode and the second non-native nucleic acid comprises the second distinguishable nucleic acid barcode.

A non-native nucleic acid that comprises a distinguishable nucleic acid barcode often comprise one or two portions that are adjacent to one or both ends of the distinguishable nucleic acid barcode. In some embodiments a portion of a non-native nucleic acid that is adjacent to an end of a distinguishable nucleic acid barcode does not comprise any nucleotides of a distinguishable nucleic acid barcode sequence. In some embodiments a portion of a non-native nucleic acid that is adjacent to an end of a distinguishable nucleic acid barcode comprises 1, 2 or 3 contiguous nucleotides of a distinguishable nucleic acid barcode sequence where the 1, 2, or 3 contiguous nucleotides are located at the end of the distinguishable nucleic acid barcode sequence. A portion of a non-native nucleic acid that is adjacent to an end of a distinguishable nucleic acid barcode often comprises 5 to 75 nucleotides, 5 to 50 nucleotides, 5 to 45 nucleotides, 5 to 40 nucleotides, 5 to 35 nucleotides, 5 to 30 nucleotides, 5 to 25 nucleotides, 5 to 20 nucleotides or 5 to 15 nucleotides that are located 5' or 3' to one end of a distinguishable nucleic acid barcode. In some embodiments a portion of a non-native nucleic acid that is adjacent to an end of a distinguishable nucleic acid barcode is located 0, 1, 2, 3, 4, 5, 6, 7, 8, 9 or 10 nucleotides from an end of a distinguishable nucleic acid barcode. In some embodiments a portion of a non-native nucleic acid that is adjacent to an end of a distinguishable nucleic acid barcode overlaps the end of a distinguishable nucleic acid barcode sequence by 1, 2 or 3 nucleotides.

Binding Pairs

In some embodiments a composition or method described herein comprises one or more binding pairs. In certain embodiments a nucleic acid comprises one or more members of binding pair. In some embodiments a binding pair comprises at least two members (e.g., molecules) that bind non-covalently to each other. Members of a binding pair often bind specifically to each other. Members of a binding pair often bind reversibly to each other, for example where the association of two members of a binding pair can be dissociated by a suitable method. Any suitable binding pair, or members thereof, can be utilized for a composition or method described herein. Non-limiting examples of a binding pair includes complementary nucleic acids, antibody/antigen, antibody/antibody, antibody/antibody fragment, antibody/antibody receptor, antibody/protein A or protein G, hapten/anti-hapten, sulfhydryl/maleimide, sulfhydryl/halo-acetyl derivative, amine/isotriocyanate, amine/succinimidyl ester, amine/sulfonyl halides, biotin/avidin, biotin/streptavidin, folic acid/folate binding protein, receptor/ligand, vitamin B12/intrinsic factor, analogues thereof, derivatives thereof, binding portions thereof, the like or combinations thereof. In some embodiments a binding pair comprises a metal or a magnetic material and a magnet. Non-limiting examples of members of a binding pair include an antibody, antibody fragment, reduced antibody, chemically modified antibody, antibody receptor, an antigen, hapten, anti-hapten, a peptide, protein, nucleic acid (e.g., double-stranded DNA (dsDNA), single-stranded DNA (ssDNA), or RNA), a nucleotide, a nucleotide analog or derivative (e.g., bromodeoxyuridine (BrdU)), an alkyl moiety (e.g., methyl moiety on methylated DNA or methylated histone), an alkanoyl moiety (e.g., an acetyl group of an acetylated protein (e.g., an acetylated histone)), an alkanoic acid or alkanoate moiety (e.g., a fatty acid), a glyceryl moiety (e.g., a lipid), a phosphoryl moiety, a glycosyl moiety, a ubiquitin moiety, lectin, aptamer, receptor, ligand, metal ion, avidin, neutravidin, biotin, B12, intrinsic factor, analogues thereof, derivatives thereof, binding portions thereof, the like or combinations thereof. For example, in certain embodiments one member of a binding pair comprises biotin, or an analogue or derivative thereof and the other member of the pair comprises avidin, or an analogue or derivative thereof. In another example, in certain embodiments one member of a binding pair comprises a suitable metal (e.g., a substrate comprising a metal, a metal nanoparticle, iron) and the other member comprises a magnet.

Linkers

In some embodiments a distinguishable identifier and/or or a member of a binding pair are indirectly associated with, or bound to, a nucleic acid by a linker. In certain embodiments a distinguishable identifier is indirectly associated with or bound to a member of a binding pair by a linker. A linker can provide a mechanism for covalently attaching a distinguishable identifier and/or a member of a binding pair to a nucleic acid or to each other. Any suitable linker can be used in a composition or method described herein. Non-limiting examples of suitable linkers include: silanes, thiols, phosphonic acid, polyethylene glycol (PEG). Methods of attaching two or more molecules using a linker are well known in the art and are sometimes referred to as "cross-linking". Non-limiting examples of crosslinking include an amine reacting with a N-Hydroxysuccinimide (NHS) ester, an imidoester, a pentafluorophenyl (PFP) ester, a hydroxymethyl phosphine, an oxiran or any other carbonyl compound; a carboxyl reacting with a carbodiimide; a sulfhydryl reacting with a maleimide, a haloacetyl, a pyridyldisulfide, and/or a vinyl sulfone; an aldehyde reacting with a hydrazine; any non-selective group reacting with diazirine and/or aryl azide; a hydroxyl reacting with isocyanate; a hydroxylamine reacting with a carbonyl compound; the like and combinations thereof.

Nucleic Acid Sequencing

In certain embodiments nucleic acids (e.g., amplicons; nucleic acids of a library; isolated, purified and/or captured nucleic acids) are analyzed by a process comprising nucleic acid sequencing. In some embodiments, nucleic acids may be sequenced. In some embodiments, a full or substantially full sequence is obtained and sometimes a partial sequence is obtained.

Any suitable method of sequencing nucleic acids can be used, non-limiting examples of which include Maxim & Gilbert, chain-termination methods, sequencing by synthesis, sequencing by ligation, sequencing by mass spectrometry, microscopy-based techniques, the like or combinations thereof. In some embodiments, a first generation technology, such as, for example, Sanger sequencing methods including automated Sanger sequencing methods, including microfluidic Sanger sequencing, can be used in a method provided herein. In some embodiments sequencing technologies that include the use of nucleic acid imaging technologies (e.g. transmission electron microscopy (TEM) and atomic force microscopy (AFM)), can be used. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation) sequencing techniques capable of sequencing DNA in a massively parallel fashion can be used for methods described herein and are collectively referred to herein as "massively parallel sequencing" (MPS) or "massively parallel nucleic acid sequencing". In some embodiments MPS sequencing methods utilize a targeted approach, where sequence reads are generated from specific chromosomes, genes or regions of interest. Specific chromosomes, genes or regions of interest are sometimes referred to herein as targeted genomic regions. In certain embodiments a non-targeted approach is used where most or all nucleic acid fragments in a sample are sequenced, amplified and/or captured randomly.

MPS sequencing sometimes makes use of sequencing by synthesis and certain imaging processes. A nucleic acid sequencing technology that may be used in a method described herein is sequencing-by-synthesis and reversible terminator-based sequencing (e.g. Illumina's Genome Analyzer; Genome Analyzer II; HISEQ 2000; HISEQ 2500 (Illumina, San Diego Calif.)). With this technology, millions of nucleic acid (e.g. DNA) fragments can be sequenced in parallel. In one example of this type of sequencing technology, a flow cell is used which contains an optically transparent slide with 8 to 16 individual lanes on the surfaces of which are bound oligonucleotide anchors (e.g., adapter primers).

Sequencing by synthesis, in some embodiments, comprises iteratively adding (e.g., by covalent addition) a nucleotide to a primer or preexisting nucleic acid strand in a template directed manner. Each iterative addition of a nucleotide is detected and the process is repeated multiple times until a sequence of a nucleic acid strand is obtained. The length of a sequence obtained depends, in part, on the number of addition and detection steps that are performed. In some embodiments of sequencing by synthesis, one, two, three or more nucleotides of the same type (e.g., A, G, C or T) are added and detected in a round of nucleotide addition. Nucleotides can be added by any suitable method (e.g., enzymatically or chemically). For example, in some embodiments a polymerase or a ligase adds a nucleotide to a primer or to a preexisting nucleic acid strand in a template directed manner. In some embodiments of sequencing by synthesis, different types of nucleotides, nucleotide analogues and/or identifiers are used. In some embodiments reversible terminators and/or removable (e.g., cleavable) identifiers are used. In some embodiments fluorescent labeled nucleotides and/or nucleotide analogues are used. In certain embodiments sequencing by synthesis comprises a cleavage (e.g., cleavage and removal of an identifier) and/or a washing step. In some embodiments the addition of one or more nucleotides is detected by a suitable method described herein or known in the art, non-limiting examples of which include any suitable imaging apparatus or machine, a suitable camera, a digital camera, a CCD (Charge Couple Device) based imaging apparatus (e.g., a CCD camera), a CMOS (Complementary Metal Oxide Silicon) based imaging apparatus (e.g., a CMOS camera), a photo diode (e.g., a photomultiplier tube), electron microscopy, a field-effect transistor (e.g., a DNA field-effect transistor), an ISFET ion sensor (e.g., a CHEMFET sensor), the like or combinations thereof. Other sequencing methods that may be used to conduct methods herein include digital PCR and sequencing by hybridization.

A suitable MPS method, system or technology platform for conducting methods described herein can be used to obtain nucleic acid sequencing reads. Non-limiting examples of MPS platforms include Illumina/Solex/HiSeq (e.g., Illumina's Genome Analyzer; Genome Analyzer II; HISEQ 2000; HISEQ), SOLiD, Roche/454, PACBIO and/or SMRT, Helicos True Single Molecule Sequencing, Ion Torrent and Ion semiconductor-based sequencing (e.g., as developed by Life Technologies), WildFire, 5500, 5500xl W and/or 5500xl W Genetic Analyzer based technologies (e.g., as developed and sold by Life Technologies, US patent publication no. US20130012399); Polony sequencing, Pyrosequencing, Massively Parallel Signature Sequencing (MPSS), RNA polymerase (RNAP) sequencing, LaserGen systems and methods, Nanopore-based platforms, chemical-sensitive field effect transistor (CHEMFET) array, electron microscopy-based sequencing (e.g., as developed by ZS Genetics, Halcyon Molecular), nanoball sequencing, and the like.

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g. fetal alleles and maternal alleles). Alleles can be enumerated to determine copy number.

In certain embodiments, sequencing by hybridization can be used. The method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, chromosome-specific sequencing is performed. In some embodiments, chromosome-specific sequencing is performed utilizing DANSR (digital analysis of selected regions). Digital analysis of selected regions enables simultaneous quantification of hundreds of loci by DNA-dependent catenation of two locus-specific oligonucleotides via an intervening 'bridge' oligonucleotide to form a PCR template. In some embodiments, chromosome-specific sequencing is performed by generating a library enriched in chromosome-specific sequences. In some embodiments, sequence reads are obtained only for a selected set of chromosomes.

Competitor Nucleic Acids

Competitor nucleic acids are often added prior to a hybridization process to reduce unwanted and non-specific hybridization events. Competitor nucleic acids can comprise repetitive nucleic acids. Repetitive endogenous nucleic acids, such as an Alu sequence or LINE sequence, are often present in a nucleic acid library. Sometimes endogenous repetitive nucleic acids can hybridize to each other resulting in contamination of a captured hybridization mixture. This type of contamination can be reduced, in part, by adding an excess of exogenous competitor nucleic acids prior to hybridization. Any suitable competitor nucleic acids can be used in a composition or method described herein. In some embodiments competitor nucleic acids comprise C0t-1 DNA which can bind Alu, LINE, and other repeat sequences present in a nucleic acid library. C0t-1 DNA can be obtained from a suitable organism and may comprise a mixture of nucleic acids from different organisms. C0t-1 DNA can be obtained from a suitable tissue of an organism. C0t-1 DNA sometimes comprises nucleic acids isolated from placenta.

Blocking Nucleic Acids

Presented herein, in some aspects, are improved blocking methods and compositions. Often, through hybridization events, unwanted nucleic acids contaminate an enriched nucleic acid pool following completion of a hybrid capture method. A large fraction of unwanted sequences are sometimes due to undesired hybridization events between identical portions of terminal adapter sequences (e.g., barcodes, portions complementary to flow cell anchors and or primers, and the like) of adapter-ligated library inserts. Sometimes unwanted library inserts can anneal to each other through their terminal adapters, thereby resulting in a "daisy chain" of otherwise unwanted DNA fragments being linked and isolated together. In this way, capture of a single desired fragment can bring along a large number of undesired fragments, which reduces the overall efficiency of an enrichment method.

In some embodiments the so called "daisy chain" effect and other unwanted hybridization events can be reduced by using blocking nucleic acids directed to hybridize to portions of non-native nucleic acids of a library (e.g., adapter sequences). Blocking oligonucleotides are known in the art and are often configured to bind to and block hybridization between barcode sequences of a library. Traditional blocking oligonucleotides are often 50 or more nucleic acids in length and are configured to hybridize to barcode sequences as well as to synthetic nucleic acids portions that flank each side of the nucleic acid barcodes. Thus traditional blocking oligonucleotides are relatively long (e.g., >50 nucleotides) so they can anneal to barcode regions and flanking non-native sequences, and to ensure a high melting temperature between the blocking oligonucleotides and their target sequences. In some embodiments, a method herein employs the use of one or more blocking nucleic acids (e.g., traditional blocking nucleic acids).

In some embodiments, for a multiplex sequencing approach where multiple adapter-ligated libraries are mixed, multiple sets of blocking nucleic acids must be synthesized, each specific for the many different adapters of each library. Accordingly, high-throughput multiplex sequencing reactions often involve 8, 10, 15, or 20 or more different barcode sequences that require the synthesis of 8, 10, 15, or 20 or more blocking oligonucleotides, each configured to bind each of the unique barcode sequences. This strategy is costly and time consuming because many different blocking oligonucleotides of relatively long lengths must be designed and synthesized for multiplex sequencing of mixed libraries.

In some embodiments a blocking nucleic acid is a U-block nucleic acid. In some embodiments a composition or method herein comprises U-block (e.g., universal blocking) nucleic acids. U-block nucleic acids of a composition can be substantially the same or substantially different. U-block nucleic acids have several advantages over traditional blocking oligos. First U-block nucleic acids do not hybridize substantially to nucleic acid barcode sequences nor are U-block nucleic acids configured to hybridize to nucleic acid barcode sequences. Thus, manipulation, capture and multiplex sequencing of complex nucleic acid libraries that contain 8, 10, 15, or 20 or more different barcode sequences does not require a U-block nucleic acid specific for each and every unique barcode sequence. Also, U-block nucleic acids are relatively short compared to traditional blocking oligonucleotides making nucleic acid synthesis of the U-block nucleic acids more economical. In certain embodiments U-block nucleic acids provided herein have a nominal, average, mean or absolute length of 45 nucleotides of less, 40 nucleotides or less, 35 nucleotides or less, 30 nucleotides or less, 25 nucleotides or less, 20 nucleotides or less, 15 nucleotides or less, or 10 nucleotides or less. In some embodiments U-block nucleic acids have a nominal, average, mean or absolute length of 8 to about 40, 8 to about 35, 8 to about 30, 8 to about 25 or 8 to about 20 nucleotides. U-block nucleic acids can comprise any suitable nucleic acid, nucleotide or nucleotide analogue. In some embodiments U-block nucleic acids are synthetic (e.g., synthesized by the hand of man). U-block nucleic acids can be oligonucleotides.

U-block nucleic acids are often configured to block unwanted hybridization and/or subsequent amplification of non-native portions of a nucleic acid library. In certain embodiments, U-block nucleic acid are configured to hybridize to synthetic nucleic acid regions (non-native nucleic acid regions) that flank a barcode nucleic acid. Accordingly, a composition herein often comprises at least two U-block nucleic acids configured to hybridize to opposing sides of a distinguishable nucleic acid barcode. Synthetic nucleic acid regions that flank barcode nucleic acid sequences are often relatively short (e.g., 45 nucleotides of less, 40 nucleotides or less, 35 nucleotides or less, 30 nucleotides or less, 25 nucleotides or less, 20 nucleotides or less, 15 nucleotides or less, or 10 nucleotides or less) and thus provide relatively short nucleic acid stretches for U-block nucleic acids to hybridize. Early prototypes of U-block nucleic acids developed by the inventors herein consisted exclusively of standard nucleotide bases and were inefficient at blocking unwanted hybridization events. By modifying some or all of the nucleic acid bases of U-block nucleic acid, the efficiency and blocking ability could be increases substantially. Therefore, in some embodiments, U-block nucleic acids are configured to comprise higher melting temperatures, in part, by inclusion of non-standard or modified nucleic acid bases that increase the Tm of the U-block nucleic acid. In some embodiments, U-block nucleic acids comprise a Tm that is higher than that of an unmodified U-block nucleic acid of similar sequence consisting of standard nucleotides chosen from guanine, cytosine, thymine, adenine and uracil. Any suitable modification can be used to increase the Tm of a U-block nucleic acids. In some embodiments U-block nucleic acids comprise modified nucleotides, nucleotide analogues and/or modified nucleotides bonds, non-limiting examples of which include locked nucleic acids (LNAs, e.g., bicyclic nucleic acids), bridged nucleic acids (BNAs, e.g., constrained nucleic acids), C5-modified pyrimidine bases (for example, 5-methyl-dC, propynyl pyrimidines, among others) and alternate backbone chemistries, for example peptide nucleic acids (PNAs), morpholinos, the like or combinations thereof. In some embodiments, bridged nucleic acids are modified RNA nucleotides. Any suitable BNA can be used in a composition or method described herein. In certain embodiments BNA monomers can comprise a five-membered, six-membered or even a seven-membered bridged structure. Non-limiting examples of new generation BNA monomers include 2',4'-BNANC[NH], 2',4'-BNANC[NMe], and 2',4'-BNANC[NBn]. Non-base modifiers can also be incorporated into a U-block nucleic acid to increase Tm (or binding affinity), non-limiting examples of which include a minor grove binder (MGB), spermine, G-clamp, a Uaq anthraquinone cap, the like or combinations thereof. More than one type of Tm-enhancing modification can be employed in a U-block nucleic acid, such as a combination of BNA nucleotide monomers and a terminal MGB group. Many methods of increasing the Tm of complementary nucleic acids are known to those of skill in the art and the use of all such modifications is considered within the scope of the inventions herein. In some embodiments U-block nucleic acids comprise melting temperatures (Tm) of at least 40° C., at least 45° C., at least 50° C., at least 55° C., at least 60° C., at least 65° C., at least 70° C., at least 75° C., or at least 80° C.

In certain embodiments, a U-block nucleic acid is configured to specifically hybridize to one or more non-native nucleic acids of a library. A non-native nucleic acid often comprises synthetic nucleic acid sequences. In some embodiments a non-native nucleic acid does not comprise genomic DNA, a gene, mRNA, cDNA or portions thereof. In some embodiments, a U-block nucleic acid is configured to specifically hybridize to one or more amplicons of a library, where the one or more amplicons comprise synthetic nucleic acids (e.g., one or more adapters sequences, capture sequences or primer binding sites). In some embodiments, a U-block nucleic acid is configured to specifically hybridize to one or more adapters, or portions thereof. In certain embodiments a U-block nucleic acid is not configured to hybridize to a library insert. In certain embodiments a U-block nucleic acid does not substantially hybridize to a library insert. In certain embodiments a U-block nucleic acid is not configured to hybridize to a nucleic acid barcode and is not complementary to a substantial portion of a barcode sequence. In certain embodiments a U-block nucleic acid does not substantially hybridize to a nucleic acid barcode or to any portion of a nucleic acid barcode.

A U-block nucleic acid often comprises or consists of a nucleic acid sequence that is substantially complementary to a non-native nucleic acid. A U-block nucleic acid is sometimes configured to specifically hybridize to one or more non-native nucleic acids of a nucleic acid library. In some embodiments each nucleic acid of a library comprises one or more (e.g., 1, 2, 3, 4 or more) non-native nucleic acids where the non-native nucleic acids are common to (e.g., shared by) each of the nucleic acids of the library. For example, a nucleic acid library can be generated from two or more samples, where nucleic acids derived from each sample comprise unique distinguishable barcode sequences incorporated into adapter sequences, and where the adapters comprise one or more (e.g., 1, 2, 3, 4, or more) identical non-native nucleic acids (e.g., synthetic nucleic acid, universal nucleic acid sequences). Non-native nucleic acids that are substantially identical and shared between nucleic acids of a library are sometimes referred to as universal nucleic acids. U-block nucleic acids are often substantially complementary to and are configured to specifically hybridize to universal nucleic acid sequences (e.g., an adapter, or portion thereof).

In some embodiments U-block nucleic acids are configured to block extension by a polymerase. In some embodiments a U-block nucleic acid is configured to block extension of the U-block nucleic acid by a polymerase. For example, U-block nucleic acids may comprise a suitable 3' chain terminator (e.g., a 2',3' dideoxynucleotide) or suitable functional group that prevents a polymerase from extending the 3' end (e.g., by forming a phosphodiester bond) of a U-block nucleic acid. Therefore, a U-block nucleic acid configured to block extension by a polymerase often comprises a suitable 3' chain terminator (e.g., a 2',3' dideoxynucleotide) or suitable functional group that prevents a polymerase from extending the 3' end of the U-block nucleic acid. Accordingly, in certain embodiments, a U-block nucleic acid is not a nucleic acid primer suitable for amplification (e.g., PCR) or extension by a polymerase.

In some embodiments a composition herein comprises one or more nucleic acid libraries (e.g., a plurality of library inserts) derived from multiple samples and 2 or more, 3 or more, 4 or more, 5 or more, 6 or more, 7 or more, 8 or more, 9 or more or 10 or more unique distinguishable barcodes. In certain embodiments, such compositions comprise no more than 4, and sometimes no more than 8 U-block nucleic acids, each configured to specifically hybridize to a non-native nucleic acid, or a portion thereof, of each nucleic acid of the library. In some embodiments, a composition herein comprises 1, 2, 3, 4, 5, 6, 7 or 8 U-block nucleic acids and/or no more than 1, 2, 3, 4, 5, 6, 7 or 8 U-block nucleic acids. In certain embodiments a composition herein comprises 2 to 4, 2 to 6, 2 to 8 or 4 to 8 U-block nucleic acids. In some embodiments, a composition herein comprises 1, 2, 3, 4, 5, 6, 7 or 8 U-block nucleic acids, where (i) each of the U-block nucleic acids is substantially complementary to a portion of a first and/or a second non-native nucleic acid, (ii) at least one of the U-block nucleic acids is configured to hybridize adjacent to a first end of a distinguishable nucleic acid barcode, (iii) at least one of the U-block nucleic acids is configured to hybridize adjacent to a second end of a distinguishable nucleic acid barcode, and (iv) each of the U-block nucleic acids does not substantially hybridize to any portion of a distinguishable nucleic acid barcode.

In some embodiments a U-block nucleic acid is configured to hybridize adjacent to an end of a distinguishable nucleic acid barcode. In some embodiments a U-block nucleic acid that is configured to hybridize adjacent to an end of a distinguishable nucleic acid barcode refers to a U-block nucleic acid that is substantially complementary to a portion of a non-native nucleic acid that is located adjacent to a distinguishable nucleic acid barcode. U-block nucleic acids are often configured to hybridize to a non-native nucleic acid of a library that includes a distinguishable nucleic acid barcode, where the U-block nucleic acids are configured to hybridize to opposing sides of the barcode sequence. Therefore when U-block nucleic acids are hybridized to a non-native nucleic acid of a library that includes a distinguishable nucleic acid barcode, the hybridized U-block nucleic acids flank the distinguishable nucleic acid barcode on both sides of the barcode. In certain embodiments, the U-block nucleic acids do not substantially hybridize to any portion of a barcode sequence. In some embodiments, a hybridized U-block nucleic acid may overlap a barcode sequence by 1, 2, 3, 4, 5 or 6 nucleotides. Therefore, in certain embodiments, a U-block nucleic acid that does not substantially hybridize to a barcode sequence, may hybridize to a small portion of a barcode sequence (e.g., 6 nucleotides or less).

In some embodiments a composition herein comprises up to four U-block nucleic acids. The U-block nucleic acids of a composition can be the same. For example, where a composition comprises four U-block nucleic acids, the nucleic acid sequence of each of the U-block nucleic acid can be substantially identical (i.e., substantially the same). In some embodiments a composition comprises four U-block nucleic acids, where the nucleic acid sequence of each of the U-block nucleic acids is substantially different.

Capture Nucleic Acids

In some embodiments a composition or method herein comprises capture nucleic acids. A capture nucleic acid often comprises a nucleic acid portion. In some embodiments a capture nucleic is configured to specifically hybridize to a target nucleic acid, where the capture nucleic acid and its hybridized target can be captured by a suitable technique (e.g. by a pull-down method). Any suitable capture nucleic acid or set of capture nucleic acids can be used for a method or composition herein. In some embodiments a capture nucleic acid is an oligonucleotide.

Capture nucleic acids are often directly or indirectly bound (e.g., covalently or non-covalently bound) to a suitable member of a binding pair. In certain embodiments a capture nucleic acid comprises a suitable member of a binding pair. In some embodiments a member of a binding pair is bound to a capture nucleic acid by a linker.

Capture nucleic acids comprising a member of a binding pair can be captured (e.g., captured by a capture method), along with their hybridized nucleic acid targets by use of a suitable capture method. A process of capturing nucleic acids (e.g., by a capture method) often provides captured nucleic acids (e.g., captured nucleic acids). The terms "captured" and "enriched" as used herein can refer to a nucleic acid or subset of nucleic acids provided that contain fewer nucleic acid species than in the sample prior to a capture method. A composition comprising captured nucleic acid may be about 50%, 60%, 70%, 80%, 90%, 91%, 92%, 93%, 94%, 95%, 96%, 97%, 98%, 99% or greater than 99% free of other (e.g., unwanted) nucleic acid species. In some embodiments captured nucleic acids comprise enriched nucleic acids. Enriched nucleic acid may comprise an amount of one or more nucleic acid species that are enriched at least 1.2-fold, 1.3-fold, 1.4-fold, 1.5-fold, 2-fold, 5-fold, 10-fold, 100-fold or 1000-fold compared to the amount of the one or more nucleic acid species prior to application of an enrichment or capture method. Non-limiting examples of capture methods include pull-down methods (e.g., a gravity pull-down method, a centrifugation pull-down method, a magnetic pull-down method), immunoprecipitation and various column purification methods. Isolation and/or purification of captured nucleic acids often involves association of a first member of a binding pair (e.g., bound to a capture nucleic acid) with a second member of the binding pair (e.g., bound to a substrate). A capture nucleic acid is sometimes bound to a first member of a binding pair that is configured to bind and/or associate strongly with a second member, where the second member is sometimes bound to a suitable substrate. In some embodiments a capture nucleic acid is bound to a first member of a binding pair that comprises a substrate. In some embodiments a capture nucleic acid is indirectly associated with a substrate (e.g., by a linker or an intermediate binding molecule, e.g., an antibody). In some embodiments a capture nucleic acid is bound to a first member of a binding pair that comprises a magnetic substrate (e.g., a magnetic bead, an iron containing bead) and the second member of the binding pair is a magnet. Magnets and magnetic materials can be used to capture (e.g., pull-down) a capture nucleic acid and its bound target.

In some embodiments nucleic acids and/or amplicons (e.g., nucleic acid and/or amplicons of a library) are contacted with capture nucleic acids. In certain embodiments a method comprises contacting a mixture comprising nucleic acids of a library, blocking nucleic acids and optionally one or more competitor nucleic acids with capture nucleic acids. Capture nucleic acids and methods of making capture nucleic acids are known in the art. In certain embodiments capture nucleic acids are used to capture a subset of nucleic acids of interest from a library of nucleic acids comprising a plurality of library inserts obtained from 2 or more, 10 or more, 50 or more or 100 or more subjects, samples or sources.

A capture nucleic acid can be a nucleic acid configured to specifically hybridize to a portion of one or more nucleic acids of a library (e.g., selected nucleic acids, target nucleic acids, nucleic acids of interest). In some embodiments a capture nucleic acid configured to specifically hybridize to a portion of one or more nucleic acids of a library is substantially complementary to a suitable portion of a nucleic acid of a library. In some embodiments a capture nucleic acid is configured to specifically hybridize to a portion of a non-native nucleic acid, or a portion thereof. In some embodiments a capture nucleic acid is configured to specifically hybridize to a portion of an adapter. In some embodiments a capture nucleic acid is configured to specifically hybridize to a portion of one or more library inserts. Capture nucleic acids can be configured to hybridize to promoters, enhancers, introns, exons, poly A segments, poly T segments, any suitable translational or transcriptional control sequences, the like or combinations thereof. A set of capture nucleic acids can be configured to specifically hybridize to a subset of genes (e.g., a set of genes of a chromosome, e.g., a set of genes that express a family of enzymes) or any subset of nucleic acids of a library. In some embodiments a set of capture nucleic acids are configured to hybridize at or near one or more genomic regions suspected of comprising genetic variation (e.g., deletions, insertions, SNPs, and the like). A nucleic acid that is configured to specifically hybridize to a second nucleic acid is often substantially complementary to the second nucleic acid. Capture nucleic acids are often substantially complementary to a portion of one or more nucleic acid targets (e.g., a subset of nucleic acids of a library).

In some embodiments a method comprises preparing a mixture comprising or consisting essentially of a library of nucleic acids, blocking nucleic acids, capture nucleic acids and optionally competitor nucleic acid where the mixture is subjected to a capture method. For example, in some embodiments streptavidin beads are added and nucleic acids of the mixture that are associated with the capture nucleic acids (e.g., hybridized to the capture nucleic acids) are recovered (e.g., by centrifugation, filtering, immunoprecipitation and/or by magnetic precipitation). In some embodiments a washing step is employed (e.g., by washing with ethanol). Captured nucleic acids (e.g., hybridized targets) can be eluted from capture nucleic acids using a suitable method.

In some embodiments certain methods or steps of a method are conducted in the absence of a binding pair (e.g., both members of a binding pair). For example, a mixture often comprises capture nucleic acids and a first member of a binding pair (e.g., bound to the capture nucleic acids), and the mixture does not comprise a second member of the binding pair (e.g., a second member configured to specifically bind to the first member). In some embodiments, nucleic acids of a library are contacted with blocking nucleic acids, capture nucleic acids comprising a first member of a binding pair, and/or competitor nucleic acid in the absence of a second member of the binding pair. In some embodiments a mixture comprising nucleic acids of a library, blocking nucleic acids, capture nucleic acids comprising a first member of a binding pair, and/or competitor nucleic acid is purified in the absence of a second member of the binding pair. In some embodiments a mixture comprising nucleic acids of a library, blocking nucleic acids, capture nucleic acids comprising a first member of a binding pair, and/or competitor nucleic acid is hybridized under suitable hybridization conditions in the absence of a second member of the binding pair.

In some embodiments a capture nucleic acid is directly or indirectly bound (e.g., covalently or non-covalently bound) to a suitable substrate. In certain embodiments a member of a binding pair is directly or indirectly bound (e.g., covalently or non-covalently bound) to a suitable substrate. Any suitable substrate can be used. In certain embodiments a substrate comprises a surface (e.g., a surface of a flow cell, a surface of a tube, a surface of a chip), for example a metal surface (e.g. steel, gold, silver, aluminum, silicon and copper). In some embodiment a substrate (e.g., a substrate surface) is coated and/or comprises functional groups and/or inert materials. In certain embodiments a substrate comprises a bead, a chip, a capillary, a plate, a membrane, a wafer (e.g., silicon wafers), a comb, or a pin for example. In some embodiments a substrate comprises a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, glass, nylon, Wang resin, Merrifield resin, metal (e.g., iron, a metal alloy, sepharose, agarose, polyacrylamide, dextran, cellulose and the like or combinations thereof. In some embodiments a substrate comprises a magnetic material (e.g., iron, nickel, cobalt, platinum, aluminum, and the like). In certain embodiments a substrate comprises a magnetic bead (e.g., DYNABEADS®, hematite, AMPure XP. Magnets can be used to purify and/or capture nucleic acids bound to certain substrates (e.g., substrates comprising a metal or magnetic material).

In certain embodiments capture nucleic acids and nucleic acids that specifically hybridize to capture nucleic acids (e.g., target nucleic acids) are captured by a suitable capture method, thereby providing captured nucleic acid. A process comprising capturing often provides enriched nucleic acids (e.g., nucleic acids enriched for target nucleic acids). Captured nucleic acids are often enriched for one or more species of nucleic acids. Captured nucleic acids can comprise one or more capture nucleic acids, nucleic acids that specifically hybridize to capture nucleic acids (e.g., captured nucleic acids of a library, target nucleic acids, enriched nucleic acids), a member of a binding pair, and/or a substrate. Nucleic acids that specifically hybridize to capture nucleic acids (target nucleic acids) can be recovered by a suitable method. For example, in some embodiments nucleic acids enriched by a capture method can be isolated by denaturing (e.g., by applying heat) or by increasing or decreasing the salt concentration of a mixture comprising captured nucleic acid. In some embodiments a capture method comprises use of a filter, membrane or column to recover enriched nucleic acids. In certain embodiments gravity and/or centrifugation is used to capture nucleic acids and/or to recover enriched nucleic acids. In certain embodiment a capture method does not employ centrifugation. In certain embodiments a magnet is used to capture and/or recover enriched nucleic acids. Nucleic acids bound to a substrate can often be washed by a suitable method to remove unbound or unwanted material. In certain embodiments the stringency of a wash solution can be adjusted by a suitable method.

Captured nucleic acids, nucleic acids that specifically hybridize to capture nucleic acids, enriched nucleic acids and/or amplicons thereof can be analyzed by a suitable method which can include a process comprising nucleic acid sequencing or mass spectrometry, for example.

Immobilization

In certain embodiments nucleic acids are immobilized (e.g., immobilized on a substrate). Nucleic acids can be immobilized by any suitable method. Nucleic acids can be immobilized to a suitable substrate or material, either directly or indirectly. Nucleic acids that are immobilized to a substrate can be covalently or non-covalently bound to a substrate. In certain embodiments, nucleic acids are reversibly immobilized to a substrate and can be dis-associated or removed from a substrate using a suitable method. In some embodiments nucleic acids that comprise a first member of a binding pair are immobilized to a substrate by binding to a second member of the binding pair that is bound or associated with the substrate. Nucleic acids can be non-specifically immobilized to a substrate, for example where the substrate comprises an anion (e.g., an anion exchange group, e.g., positively charged functional groups). In certain embodiments, nucleic acid are immobilized to a substrate by magnetic attractive forces. For example, a nucleic acid may comprise a magnetic material (e.g., a metal) and the nucleic acid can be immobilized to a substrate (e.g., a portion of tube, a surface) by use of a magnet. In certain embodiments a magnet is not in solution and/or is not in direct contact with a nucleic acid comprising a magnetic material. In certain embodiment a magnet is in solution and makes direct contact with a magnetic material associated with a nucleic acid. In some embodiments nucleic acids are immobilized by formation of a covalent bond, for example by cross-linking a functional group of a nucleic acid (e.g., a functional group of a nucleic acid analogue) to a substrate comprising a reactive group. In some embodiments, nucleic acids (e.g., amplicons, nucleic acids of a library, target nucleic acids) are immobilized to a substrate by hybridizing (e.g., specifically hybridizing, annealing) to another nucleic acid that is bound (e.g., covalently or non-covalently) to a substrate.

Nucleic acids can be immobilized at any suitable step of a method described herein. In some embodiments nucleic acids are immobilized to a flow cell (e.g., a surface of a flow cell) or to an array (e.g., a chip). In certain embodiments, a method described herein does not comprise immobilizing nucleic acids to a flow cell or chip. In certain embodiments, a method described herein does not comprise immobilizing nucleic acids to a flow cell or chip until after a capture method. In certain embodiments, a method described herein does not comprise immobilizing nucleic acids to a flow cell or chip prior to analysis of the nucleic acids, for example by nucleic acid sequencing. In some embodiments, nucleic acids of a library (e.g., amplicons of a library) are ligated to adapters, contacted with blocking nucleic acids, contacted with capture nucleic acids, contacted with competitor nucleic acids, purified and/or hybridized (e.g., subjected to a denaturation and annealing process) and are not immobilized to a flow cell, an array or chip before or during any or all of the aforementioned processes. In certain embodiments, nucleic acids of a library (e.g., amplicons of a library) are ligated to adapters, contacted with blocking nucleic acids, contacted with capture nucleic acids, contacted with competitor nucleic acids, purified and/or hybridized (e.g., subjected to a denaturation and annealing process) in the absence of a flow cell, array or chip.

Other Nucleic Acid Methods

In some embodiments a method herein comprises preparing a mixture for subsequent hybridization and/or capture. In certain embodiments a mixture is prepared comprising contacting nucleic acids of one or more nucleic acid libraries (e.g., amplicons) with one or more blocking nucleic acids, one or more capture nucleic acids and/or one or more competitor nucleic acids. In some embodiments the mixture is prepared prior to denaturing or hybridizing. A mixture prepared by a method described herein can comprise one or more nucleic acid libraries (e.g., amplicons), one or more blocking nucleic acids, one or more capture nucleic acids and/or one or more competitor nucleic acids. A mixture prepared by a method described herein may comprise or consist essentially of a library of nucleic acids, blocking nucleic acids and capture nucleic acids. In certain embodiments the prepared mixture comprises or consists essentially of a library of nucleic acids, blocking nucleic acids, capture nucleic acids and competitor nucleic acid. A prepared mixture that consists essentially of nucleic acids may contain water, EDTA, PEG, NaCl and/or a buffer (e.g., Tris or HEPES). In some embodiments a mixture that consists essentially of nucleic acids does not contain a hybridization buffer. In certain embodiments a method of preparing a mixture of nucleic acids does not comprise adding a hybridization buffer. In certain embodiments a prepared mixture that consists essentially of nucleic acids does contain calcium or magnesium salts. In some embodiments a prepared mixture of nucleic acids does not contain calcium or magnesium salts, a detergent (e.g., SDS), Ficoll, BSA, or polyvinylpyrrolidone. In some embodiments a mixture that consists essentially of nucleic acids does not contain a detergent (e.g., SDS), Ficoll, BSA or polyvinylpyrrolidone.

In some embodiments, a mixture is prepared as described herein and the mixture in not heated until after the nucleic acids of the mixture are purified. For example, a mixture is not heated to a temperature greater than about 70° C., 75° C., 80° C., 85° C., 90° C., or greater than 95° C. prior to purification of nucleic acids from the mixture and/or until after the nucleic acids of the mixture are purified.

Genetic Variations and Medical Conditions

The presence or absence of a genetic variance can be determined using a composition or method, described herein. A genetic variation generally is a particular genetic phenotype present in certain individuals, and often a genetic variation is present in a statistically significant sub-population of individuals. In some embodiments, a genetic variation is a chromosome abnormality (e.g., aneuploidy, duplication of one or more chromosomes, loss of one or more chromosomes), partial chromosome abnormality or mosaicism (e.g., loss or gain of one or more segments of a chromosome), a translocation or an inversion. Non-limiting examples of genetic variations include one or more deletions, duplications, insertions, mutations, polymorphisms (e.g., single-nucleotide polymorphisms), fusions, repeats (e.g., short tandem repeats), the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 50,000 kilobases (kb) in length (e.g., about 10 bp, 50 bp, 100 bp, 500 bp, 1 kb, 5 kb, 10 kb, 50 kb, 100 kb, 500 kb, 1000 kb, 5000 kb or 10,000 kb in length).

In certain embodiments a genetic variation, for which the presence or absence is identified for a subject, is sometimes associated with a medical condition. Non-limiting examples of medical conditions include those associated with intellectual disability (e.g., Down Syndrome), aberrant cell-proliferation (e.g., cancer), Non-Hodgkin's lymphoma, myelodysplastic syndrome, William's syndrome, Langer-Giedon syndrome, Alfi's syndrome, Rethore syndrome, Jacobsen Syndrome, retinoblastoma, Smith-Magenis, Edwards Syndrome, papillary renal cell carcinomas, DiGeorge syndrome, Angelman syndrome, Cat-Eye Syndrome, Familial Adenomatous Polyposis, Miller-Dieker syndrome, presence of a micro-organism nucleic acid (e.g., virus, bacterium, fungus, yeast), and preeclampsia.

EXAMPLES

The examples set forth below illustrate certain embodiments and do not limit the technology.

Example 1: Workflow Advances in Hybridization Capture Workflow for Efficiency, Cost Reduction, and Data Quality Improvements The new and improved methods exemplified herein have provided the following advantages.
1. Avoidance of vacuum- and heat-based concentration of reaction mixes using zero-volume concentration via magnetic beads
2. Concentration of DNA baits for increased reaction kinetics
3. Concentration of short nucleic acids for workflow improvement
4. Denaturation of a completed hybridization reaction
5. Efficient and automatable streptavidin bead manipulation Traditional protocols for hybridization capture assay (e.g., Roche-NimbleGen SeqCap EZ Library SR User's Guide, website pdf document accessed Aug. 20, 2014 at: http://www.nimblegen.com/products/lit/06588786001_SeqCapEZLibrarySR_UGuide_v4p2.pdf) have required many operations that are absolutely not compatible with high throughput genetic testing methods. The protocols provided herein have resulted in dramatically increases in efficiency and data quality while reducing costs.

Setup of a traditional hybridization reaction have involved combining three components (DNA library, blocking oligonucleotides, and human Cot-1 DNA), followed by a required evaporation step to remove all liquid via simultaneous centrifugation of open tubes under vacuum and heat (known to those in the field as "Speed-vac"). The evaporation step was required, in part, because the hybridization buffers must be added at high concentrations and additional dilution of the original three components was unacceptable. The evaporation step was particularly slow (>1 hour), was prone to cross contamination, and was not generally compatible with high-throughput processing.

See the Table 1 below for a description of the novel hybridization method.

TABLE 1

| Novel Method | Advantages |
| --- | --- |
| Mix library, blocking oligos, DNA baits and optionally Cot-1 competitor DNA | DNA biotinylated baits are included in the mixture. |
| Concentrate mixture using AMPureXP beads | Avoids contamination; completed in less than 1 hour; can be automated and performed by a robotic apparatus. Method does not require heat or a vacuum. |
| Mixture resuspended in 5 µl 2x hybridization buffer, 2 µl of Hyb Component A (Roche) and 3 µl water. | Provides a concentrated suspension of all components. |
| Denature at 95 for 10 min., immediately ramp to 47° C. | Provides for a one step denaturation/hybridization. Provides for faster processing since baits are not added in a separate step. |
| Incubate 47° C. for 16 hours. | Reduces capture incubation time by as much as 48 hours. |

The first aspect of the novel methods described herein has incorporated the use of a magnetic bead capable of binding nucleic acids non-specifically to quickly concentrate the nucleic acid materials onto a magnetic bead "pellet", which was then resuspended in a hybridization buffer at the appropriate concentrations. This also improved process has maintained the same amount of baits in a reduced final volume which improved reaction kinetics while maintaining concentrations of all components.

The second aspect of the novel methods described herein has included the biotinylated DNA capture baits into the concentration reaction.

The third aspect of the novel method has involved modifying the purification conditions to ensure efficient purification of the short single-stranded DNA baits, and short-single stranded blocking oligos (in addition to the longer double stranded library, and Cot-1 DNA). AMPureXP beads were used for concentration, at a modified ratio of 2 parts beads to 1 part reaction (manufacturer recommends 1.8:1), which resulted in more effective binding of short nucleic acids (typically removed by the 1.8:1 ratio).

The fourth aspect of the novel method has involved denaturing the reaction mixture in its complete format with all components present. Traditional protocols have recommend that the DNA, Cot-1 and the blocking oligos be denatured at 95° C., followed by unsealing/opening of the plate to allow an additional transfer of the biotinylated DNA baits. Results obtained from the novel methods presented herein have demonstrated that, in addition to including the baits in the concentration reaction (second aspect above), that the entire reaction mixture that includes the baits, can be denatured at 95° C. together, followed by an immediate ramp to hybridization temperature (47° C.). Surprisingly, this method has not resulted in a loss of overall blocking efficiency and has not resulted in a decrease in efficiency of capture hybridization. Contrarily, the method has resulted in an increase in the yield of library nucleic acids captured. This provided a dramatic workflow improvement as it has eliminated multiple interactions with the thermocycler, which is not efficient, and has eliminated the high risk of cross contamination caused by unsealing a plate of patient samples.

The fifth aspect of the novel method has further improved the capture of nucleic acids of a library using streptavidin capture beads and biotinylated baits. Traditional protocols have required removal of the supernatant from the streptavidin beads, leaving behind a pellet of beads, which has to be resuspended using the hybridization reaction (10-15 µl) which comprises nucleic acids of the library. This process has proved problematic and difficult due to the large quantity of streptavidin beads that are resuspended in a relatively small volume. To overcome the problems associated the traditional process and to enable automation, the pellet of streptavidin beads was resuspended in 10 µl of hybridization buffer (e.g., with vigorous vortexing and pipetting), and then added to the 10-15 µl of the hybridization reaction. This maintained the buffer composition of the final reaction and enabled complete automation.

Overall, the novel methods presented herein were completed in less time than required for traditional protocols (e.g., at least 2 days shorter), have required less steps and less handling of samples, have unexpectedly resulted in higher quality data (percent on target of >90% versus 70-80% using the traditional protocol), have allowed complete and efficient automation, and have provided safer treatment of patient DNA samples. In addition, DNA libraries were not subjected to prolonged periods of heat, for example from speed-vac drying and prolonged hybridization periods, which can result in degradation of a nucleic acids of a library.

Example 2: Examples of Embodiments

The examples set forth below illustrate certain embodiments and do not limit the technology.

A1. A composition for use in massive parallel nucleic acid sequencing comprising:
  a) a library of nucleic acids comprising a plurality of library inserts obtained from one or more samples and at least eight distinguishable nucleic acid barcodes, each nucleic acid barcode comprising a first end and a second end, and each nucleic acid of the library comprising (i) at least one of the library inserts, (ii) a first non-native nucleic acid, (iii) a second non-native nucleic acid and (iv) no more than two of the distinguishable nucleic acid barcodes, wherein
  the first non-native nucleic acid and the second non-native nucleic acid are located on opposing sides of the at least one library insert, and
  the first non-native nucleic acid and/or the second non-native nucleic acid comprise the no more than two distinguishable nucleic acid barcodes; and
  b) no more than four U-block nucleic acids, wherein (i) each of the U-block nucleic acids is substantially complementary to a portion of the first and/or the second non-native nucleic acids, (ii) at least one of the U-block nucleic acids is configured to hybridize adjacent to the first end of each of the distinguishable nucleic acid barcodes, (iii) at least one of the U-block nucleic acids is configured to hybridize adjacent to the second end of each of the distinguishable nucleic acid barcodes, and (iv) each of the U-block nucleic acids does not substantially hybridize to a portion of the at least eight distinguishable nucleic acid barcodes.

A2. The composition of embodiment A1, comprising one or more capture nucleic acids, wherein
  (i) the capture nucleic acids comprise a member of a binding pair, and
  (ii) each of the capture nucleic acids is configured to specifically hybridize to a subset of the one or more library inserts.

A3. The composition of embodiment A1 or A2, wherein the one or more samples are obtained from one or more species.

A3.1. The composition of any one of embodiments A1 to A3, comprising four or more samples.

A3.2. The composition of any one of embodiments A1 to A3, comprising eight or more samples.

A4. The composition of any one of embodiments A3 to A3.2, wherein the first and second non-native nucleic acids are not endogenous to a genome of the one or more species.

A5. The composition of any one of embodiments A1 to A4, wherein the one or more samples are obtained from one or more tissues.

A6. The composition of any one of embodiments A1 to A4, wherein the one or more samples are obtained from one or more mammals.

A7. The composition of embodiment A6, wherein the one or more mammals are human.

A8. The composition of embodiment A6 or A7, wherein the first and second non-native nucleic acids are not endogenous to a genome of the one or more mammals.

A9. The composition of any one of embodiments A1 to A8, comprising ten or more distinguishable nucleic acid barcodes.

A10. The composition of any one of embodiments A1 to A9, wherein the one or more library inserts are obtained from eight or more samples.

A11. The composition of any one of embodiments A1 to A10, wherein each nucleic acid of the library comprises two of the distinguishable nucleic acid barcodes.

A12. The composition of embodiment A11, wherein the first non-native nucleic acid comprises a first distinguishable nucleic acid barcode and the second non-native nucleic acid comprises a second distinguishable nucleic acid barcode.

A13. The composition of embodiment A12, wherein each of the U-block nucleic acids are configured to block extension by a polymerase.

A14. The composition of any one of embodiments A1 to A13, wherein the first and second non-native nucleic acids are synthetic nucleic acids.

A15. The composition of any one of embodiments A1 to A14, wherein the first and second non-native nucleic acids are not substantially identical.

A16. The composition of any one of embodiments A1 to A15, wherein the first and second non-native nucleic acids comprise adapter nucleic acids.

A17. The composition of any one of embodiments A1 to A16, wherein the one to four U-block nucleic acids comprise a length of 10 to 40 nucleotides.

A18. The composition of any one of embodiments A1 to A17, wherein the no more than four U-block nucleic acids comprise a length of 10 to 30 nucleotides.

A19. The composition of any one of embodiments A1 to A18, wherein the no more than four U-block nucleic acids comprise a length of 10 to 20 nucleotides.

A20. The composition of any one of embodiments A1 to A19, wherein the no more than four U-block nucleic acids comprise locked nucleic acids.

A21. The composition of any one of embodiments A1 to A20, wherein the no more than four U-block nucleic acids comprise bridged nucleic acids.

A22. The composition of any one of embodiments A1 to A21, wherein the no more than four U-block nucleic acids comprise a melting temperature of between about 65° C. and about 90° C.

A23. The composition of any one of embodiments A1 to A22, wherein the no more than four U-block nucleic acids comprises a melting temperature of at least 65° C.

A24. The composition of any one of embodiments A1 to A22, wherein the no more than four U-block nucleic acids comprises a melting temperature of at least 75° C.

A25. The composition of any one of embodiments A1 to A24, wherein the composition comprises four U-block nucleic acids.

A26. The composition of any one of embodiments A1 to A25, wherein the first non-native nucleic acid comprises one of the at least eight distinguishable nucleic acid barcodes, a portion substantially complementary to a first U-block nucleic acid, and a portion substantially complementary to a second U-block nucleic acid, wherein the first U-block nucleic acid is configured to hybridize adjacent to the first end of the one distinguishable nucleic acid barcode and the second U-block nucleic acid is configured to hybridize adjacent to the second end of the one distinguishable nucleic acid barcode.

A27. The composition of any one of embodiments A1 to A26, wherein the second non-native nucleic acid comprises one of the at least eight distinguishable nucleic acid barcodes, a portion substantially complementary to a third U-block nucleic acid, and a portion substantially complementary to a fourth U-block nucleic acid, wherein the third U-block nucleic acid is configured to hybridize adjacent to the first end of the one distinguishable nucleic acid barcode and the fourth U-block nucleic acid is configured to hybridize adjacent to the second end of the one distinguishable nucleic acid barcode.

A28. The composition of any one of embodiment A1 to A27, wherein the no more than four U-block nucleic acids are not substantially complementary to the at least eight distinguishable nucleic acid barcodes.

A29. The composition of any one of embodiments A1 to A28, comprising competitor nucleic acids.

A29.1. The composition of embodiment A29, wherein the competitor nucleic acids comprise placental nucleic acid.

A30. The composition of embodiment A29, wherein the competitor nucleic acids comprise repetitive nucleic acids.

A31. The composition of embodiment A30, wherein the repetitive nucleic acids are human.

A32. The composition of embodiment A30, wherein the competitor nucleic acids comprise at least 60% of the repetitive nucleic acid.

A33. The composition of embodiment A30, wherein the competitor nucleic acids comprise synthetic repetitive nucleic acid.

A34. The composition of embodiment A29, wherein the competitor nucleic acids comprise C0t-1 nucleic acid.

A35. The composition of any one of embodiments A2 to A34, wherein the member of the binding pair comprises a biotin, an antigen, a hapten, an antibody or a portion thereof.

A36. The composition of embodiment A35, wherein the member of a binding pair comprises biotin.

A37. The composition of embodiment A35, wherein the member of the binding pair comprises a DNA binding protein recognition sequence or a portion thereof.

A38. The composition of any one of embodiments A1 to A37, wherein the no more than four U-block nucleic acids are single stranded.

A39. The composition of any one of embodiments A1 to A38, wherein the no more than four U-block nucleic acids comprise a chain terminator.

A40. The composition of any one of embodiments A1 to A39, wherein the no more than four U-block nucleic acids comprise an inverted repeat.

A41. The composition of any one of embodiments A1 to A40, wherein the library of nucleic acids comprises single stranded nucleic acids.

A42. The composition of any one of embodiments A1 to A41, wherein the library of nucleic acids comprises amplicons.

A43. The composition of any one of embodiments A1 to A42, wherein the plurality of library inserts comprise genomic nucleic acid.

A44. The composition of any one of embodiments A1 to A43, wherein the no more than four U-block nucleic acids do not comprise a degenerate nucleotide base.

A45. The composition of embodiments A44, wherein the degenerate nucleotide base is 3-nitropyrrole, 5-nitroindole, an analogue or derivative thereof.

A46. The composition of embodiment A45, wherein the degenerate nucleotide base is inosine, 2'-deoxyinosine, an analogue or derivative thereof.

A47. The composition of any one of embodiments A1 to A46, comprising a first, second, third and fourth U-block nucleic acid, wherein the first and second U-block nucleic acids are substantially complementary to a portion of the first non-native nucleic acid and the third and fourth U-block nucleic acids are substantially complementary to a portion of the second non-native nucleic acid.

A48. The composition of any one of embodiments A1 to A47, wherein the no more than four U-block nucleic acids comprise substantially different nucleic acid sequences.

B1. A method of analyzing a nucleic acid library comprising:
a) obtaining a library of nucleic acids comprising a plurality of library inserts obtained from one or more samples and at least eight distinguishable nucleic acid barcodes, each nucleic acid barcode comprising a first end and a second end, and each nucleic acid of the library comprising (i) at least one of the library inserts, (ii) a first non-native nucleic acid, (iii) a second non-native nucleic acid and (iv) no more than two of the distinguishable nucleic acid barcodes, wherein
the first non-native nucleic acid and the second non-native nucleic acid are located on opposing sides of the at least one library insert, and
the first non-native nucleic acid and/or the second non-native nucleic acid comprise the no more than two distinguishable nucleic acid barcodes;
b) preparing a first mixture comprising contacting the library of nucleic acids with no more than four U-block nucleic acids, wherein each of the U-block nucleic acids is substantially complementary to a portion of the first and/or the second non-native nucleic acids, at least one of the U-block nucleic acids is configured to hybridize adjacent to the first end of each of the distinguishable nucleic acid barcodes and at least one of the U-block nucleic acids is configured to hybridize adjacent to the second end of each of the distinguishable nucleic acid barcodes;
c) preparing a second mixture comprising contacting the first mixture with one or more capture nucleic acids, wherein
(i) the capture nucleic acids comprise a first member of a binding pair, and
(ii) each of the capture nucleic acids is configured to specifically hybridize to a subset of the one or more library inserts;
d) contacting the second mixture with a second member of the binding pair, thereby providing isolated nucleic acid;
e) contacting the isolated nucleic acid with a set of primers under amplification conditions, thereby providing amplicons; and
f) analyzing the amplicons.

B2. The method of embodiment B1, wherein the one or more samples are obtained from one or more species.

B3. The method of embodiment B2, wherein library inserts are obtained from four or more samples.

B4. The method of embodiment B2, wherein library inserts are obtained from eight or more samples.

B5. The method of any one of embodiments B1 to B4, wherein the one or more samples are obtained from one or more tissues.

B6. The method of any one of embodiments B1 to B5, wherein the one or more samples are obtained from one or more mammals.

B7. The method of embodiment B6, wherein the one or more mammals are human.

B8. The method of embodiment B6 or B7, wherein the first and second non-native nucleic acids are not endogenous to a genome of the one or more mammals.

B9. The method of any one of embodiments B1 to B8, the library of inserts comprises ten or more distinguishable nucleic acid barcodes.

B10. The method of any one of embodiments B1 to B9, wherein the first non-native nucleic acid comprises a first distinguishable nucleic acid barcode and the second non-native nucleic acid comprises a second distinguishable nucleic acid barcode.

B11. The method of any one of embodiments embodiment B1 to B10, wherein each nucleic acid of the library comprises two of the distinguishable nucleic acid barcodes.

B12. The method of any one of embodiments B1 to B11, wherein each of the U-block nucleic acids are configured to block extension by a polymerase.

B13. The method of any one of embodiments B1 to B12, wherein the first and second non-native nucleic acids are synthetic nucleic acids.

B14. The method of any one of embodiments B1 to B13, wherein the first and second non-native nucleic acids are not substantially identical.

B15. The method of any one of embodiments B1 to B14, wherein the first and second non-native nucleic acids comprise adapter nucleic acids.

B16. The method of any one of embodiments B1 to B15, wherein the one to four U-block nucleic acids comprise a length of 10 to 40 nucleotides.

B17. The method of any one of embodiments B1 to B16, wherein the no more than four U-block nucleic acids comprise a length of 10 to 30 nucleotides.

B18. The method of any one of embodiments B1 to B17, wherein the no more than four U-block nucleic acids comprise a length of 10 to 20 nucleotides.

B19. The method of any one of embodiments B1 to B18, wherein the no more than four U-block nucleic acids comprise locked nucleic acids.

B20. The method of any one of embodiments B1 to B19, wherein the no more than four U-block nucleic acids comprise bridged nucleic acids.

B21. The method of any one of embodiments B1 to B20, wherein the no more than four U-block nucleic acids comprise a melting temperature of at least 65° C.

B22. The method of any one of embodiments B1 to B21, wherein the no more than four U-block nucleic acids comprise a melting temperature of at least 75° C.

B23. The method of any one of embodiments B1 to B22, wherein the no more than four U-block nucleic acids comprise a melting temperature of between about 65° C. and about 90° C.

B24. The method of any one of embodiments B1 to B23, wherein the first non-native nucleic acid comprises one of the at least eight distinguishable nucleic acid barcodes, a portion substantially complementary to a first U-block nucleic acid, and a portion substantially complementary to a second U-block nucleic acid, wherein the first U-block nucleic acid is configured to hybridize adjacent to the first end of the one distinguishable nucleic acid barcode and the second U-block nucleic acid is configured to hybridize adjacent to the second end of the one distinguishable nucleic acid barcode.

B25. The method of any one of embodiments B1 to B24, wherein the second non-native nucleic acid comprises one of the at least eight distinguishable nucleic acid barcodes, a portion substantially complementary to a third U-block nucleic acid, and a portion substantially complementary to a fourth U-block nucleic acid, wherein the third U-block nucleic acid is configured to hybridize adjacent to the first end of the one distinguishable nucleic acid barcode and the fourth U-block nucleic acid is configured to hybridize adjacent to the second end of the one distinguishable nucleic acid barcode.

B26. The method of any one of embodiments B1 to B25, wherein the no more than four U-block nucleic acids are not substantially complementary to the at least eight distinguishable nucleic acid barcodes.

B27. The method of embodiment B26, wherein the no more than four U-block nucleic acids do not substantially hybridize to a portion of the at least eight distinguishable nucleic acid barcodes.

B28. The method of any one of embodiments B1 to B27, comprising prior to c), contacting the first mixture with competitor nucleic acids.

B28.1. The method of embodiment B28, wherein the competitor nucleic acids comprise placental nucleic acid.

B29. The method of embodiment B28 or B28.1, wherein the competitor nucleic acids comprise repetitive nucleic acids.

B30. The method of embodiment B29, wherein the repetitive nucleic acids are human.

B31. The method of embodiment B29, wherein the competitor nucleic acids comprise at least 60% of the repetitive nucleic acid.

B32. The method of embodiment B1 wherein the competitor nucleic acids comprise synthetic nucleic acid.

B33. The method of embodiment B1, wherein the competitor nucleic acids comprise C0t-1 nucleic acid.

B34. The method of embodiment B1, wherein the first member of the binding pair comprises a biotin, an antigen, a hapten, an antibody or a portion thereof.

B35. The method of embodiment B34, wherein the first member of the binding pair comprises biotin.

B36. The method of embodiment B1, wherein the first member of the binding pair comprises a DNA binding protein recognition sequence or a portion thereof.

B37. The method of any one of embodiments B1 to B36, wherein the no more than four U-block nucleic acids are single stranded.

B38. The method of any one of embodiments B1 to B37, wherein the no more than four U-block nucleic acids comprise a chain terminator.

B39. The method of any one of embodiments B1 to B38, wherein the no more than four U-block nucleic acids comprise an inverted repeat.

B40. The method of any one of embodiments B1 to B39, wherein the library of nucleic acids comprises single stranded nucleic acid.

B41. The method of any one of embodiments B1 to B40, wherein the library of nucleic acids comprises amplicons.

B42. The method of any one of embodiments B1 to B41, wherein the plurality of library inserts comprise genomic nucleic acid.

B43. The method of any one of embodiments B1 to B42, wherein the no more than four U-block nucleic acids do not comprise a degenerate nucleotide base.

B44. The method of embodiments B43, wherein the degenerate nucleotide base is 3-nitropyrrole, 5-nitroindole, an analogue or derivative thereof.

B45. The method of embodiments B43, wherein the degenerate nucleotide base is inosine, 2'-deoxyinosine, an analogue or derivative thereof.

B46. The method of embodiment B1, wherein the first member of the binding pair comprises a biotin, an antigen, a hapten, an antibody or a portion thereof.

B47. The method of embodiment B1, wherein the first member of the binding pair comprises biotin.

B48. The method of embodiment B1, wherein the first member of the binding pair comprises a DNA binding protein recognition sequence or a portion thereof.

B49. The method of any one of embodiments B1 to B48, comprising hybridizing the isolated nucleic acids under hybridization conditions.

B50. The method of embodiment B1, wherein the amplification conditions comprise a heat-stable polymerase.

B51. The method of embodiment B1, wherein the amplification conditions comprise a polymerase chain reaction.

B52. The method of embodiment B1, wherein the capture nucleic acids are configured to specifically hybridize to a portion of an exon.

B53. The method of embodiment B1, wherein the capture nucleic acids are configured to specifically hybridize to a portion of a chromosome.

B54. The method of embodiment B1, wherein the second member of the binding pair comprises avidin, protein A, protein G, an antibody, or a binding portion thereof.

B55. The method of embodiment B1, wherein the second member of the binding pair comprises avidin, or a portion thereof.

B56. The method of embodiment B1, wherein the second member of the binding pair comprises a substrate.

B57. The method of embodiment B56, wherein the substrate comprises a magnetic compound.

B58. The method of embodiment B56, wherein the substrate comprises a bead.

B59. The method of embodiment B56, wherein the substrate comprises polystyrene, polycarbonate or agarose.

B60. The method of embodiment B56, wherein the substrate comprises a magnetic bead.
B61. The method of embodiment B1, wherein the contacting in (d) comprises centrifugation.
B62. The method of embodiment B1, wherein the contacting in (d) comprises use of a magnet.
B63. The method of embodiment B1, wherein the analyzing comprising providing sequence reads.
B64. The method of embodiment B63, wherein the sequence reads are obtained by a method comprising massive parallel sequencing.
B65. The method of embodiment B63, wherein the sequence reads are obtained by a method comprising pair-end sequencing.
B66. The method of any one of embodiments B1 to B65, wherein the no more than four U-block nucleic acids comprise a first, second, third and fourth U-block nucleic acid, wherein the first and second U-block nucleic acids are substantially complementary to a portion of the first non-native nucleic acid and the third and fourth U-block nucleic acids are substantially complementary to a portion of the second non-native nucleic acid.
B67. The method of any one of embodiments B1 to B66, wherein the no more than four U-block nucleic acids comprise substantially different nucleic acid sequences.
C1. A method of analyzing a nucleic acid library comprising:
  a) obtaining a library of nucleic acids comprising a first set of amplicons, wherein each amplicon comprises a first non-native nucleic acid and a second non-native nucleic acid, one or more distinguishable identifiers, and a library insert obtained from one of one or more samples, wherein the library insert is located between the first and the second non-native nucleic acids;
  b) preparing a mixture comprising contacting the library of nucleic acids with one or more blocking nucleic acids and capture nucleic acids, wherein
    (i) the one or more blocking nucleic acids are configured to specifically hybridize to a portion of the first and second non-native nucleic acids,
    (ii) the capture nucleic acids comprise a first member of a binding pair, and
    (ii) the capture nucleic acids are configured to specifically hybridize to a subset of amplicons of the first set;
  c) purifying the mixture, thereby providing purified nucleic acid, wherein the purified nucleic acid comprises the library of nucleic acids, the one or more blocking nucleic acids, and the capture nucleic acids;
  d) hybridizing the purified nucleic acid under hybridization conditions;
  e) capturing the capture nucleic acids, thereby providing captured nucleic acid;
  f) contacting the captured nucleic acid with a set of primers under amplification condition, thereby providing a second set of amplicons; and
  g) analyzing the second set of amplicons.
C2. The method of embodiment C1, wherein the one or more samples are obtained from a human.
C3. The method of embodiment C2, wherein the first nucleic acid and the second nucleic acid are not endogenous to the human.
C4. The method of any one of embodiments C1 to C3, wherein the one or more samples are obtained from a tissue selected from breast tissue, colon tissue, pancreatic tissue, placenta, or epithelial tissue.
C5. The method of any one of embodiments C1 to C3, wherein the one or more samples are obtained from blood.
C6. The method of embodiment C5, wherein the one or more samples are obtained from circulating blood cells.
C7. The method of any one of embodiments C2 to C6, wherein the human is a fetus.
C8. The method of embodiment C5, wherein the one or more samples comprise circulating cell-free nucleic acid.
C9. The method of any one of embodiments C1 to C8, wherein the amplification conditions comprise a heat-stable polymerase.
C10. The method of any one of embodiments C1 to C9, wherein the amplification conditions comprise a polymerase chain reaction.
C11. The method of any one of embodiments C1 to C10, wherein the preparing in (b) comprises contacting the nucleic acids of the library with competitor nucleic acids.
C12. The method of embodiment C11, wherein the competitor nucleic acids comprise placental nucleic acid.
C13. The method of embodiment C11, wherein the competitor nucleic acids comprise repetitive nucleic acids.
C14. The method of embodiment C13, wherein the repetitive nucleic acids are derived from a human.
C15. The method of embodiment C13, wherein the competitor nucleic acids comprise at least 60% or more of the repetitive nucleic acids.
C16. The method of embodiment C11, wherein the competitor nucleic acids comprise synthetic nucleic acid.
C17. The method of embodiment C11, wherein the competitor nucleic acids comprise C0t-1 nucleic acid.
C18. The method of any one of embodiments C1 to C17, wherein the capture nucleic acids are configured to specifically hybridize to a portion of the library insert.
C19. The method of any one of embodiments C1 to C18, wherein the one or more blocking nucleic acids are configured to specifically hybridize to a portion of the first non-native nucleic acid and/or the second non-native nucleic acid.
C20. The method of any one of embodiments C1 to C18, wherein the one or more blocking nucleic acids are configured to prevent extension of the blocking nucleic acids by a polymerase.
C21. The method of any one of embodiments C1 to C20, wherein the one or more blocking nucleic acids comprise a chain terminator.
C22. The method of any one of embodiments C1 to C21, wherein the one or more blocking nucleic acids comprise an inverted repeat.
C23. The method of any one of embodiments C1 to C22, wherein the capture nucleic acids are configured to specifically hybridize to a portion of an exon.
C24. The method of any one of embodiments C1 to C23, wherein the capture nucleic acids are configured to specifically hybridize to a portion of a chromosome.
C25. The method of embodiment C24, wherein the capture nucleic acids are configured to specifically hybridize to a portion of a library insert comprising a genetic variation.
C26. The method of any one of embodiments C1 to C26, wherein the first member of the binding pair comprises a biotin, an antigen, a hapten, an antibody or a portion thereof.

C27. The method of embodiment C26, wherein the first member of a binding pair comprises biotin.

C28. The method of any one of embodiments C1 to C27, wherein the first member of the binding pair comprises a CNC binding protein recognition sequence or a portion thereof.

C29. The method of any one of embodiments C1 to C28, wherein the capturing in (e) comprises contacting the mixture with a second member of a binding pair.

C30. The method of embodiment C29, wherein the second member of the binding pair comprises avidin, protein A, protein G, an antibody, or a binding portion thereof.

C31. The method of embodiment C30, wherein the second member of the binding pair comprises avidin, or a portion thereof.

C32. The method of any one of embodiments C29 to C31, wherein the second member of the binding pair comprises a substrate.

C33. The method of embodiment C32, wherein the substrate comprises a magnetic compound.

C34. The method of embodiment C32, wherein the substrate comprises a bead.

C35. The method of embodiment C32, wherein the substrate comprises polystyrene, polycarbonate or agarose.

C36. The method of embodiment C32, wherein the substrate comprises a metal.

C37. The method of any one of embodiments C1 to C36, wherein capturing in (e) comprises recovering the captured nucleic acids by a method comprising centrifugation.

C38. The method of any one of embodiments C1 to C37, wherein capturing in (e) comprises recovering the captured nucleic acids by a method comprising use of a magnet.

C39. The method of any one of embodiments C1 to C38, wherein the hybridization conditions comprise denaturing.

C40. The method of any one of embodiments C1 to C39, wherein the hybridizing in (d) comprises hybridizing the captured nucleic acids to a portion of one or more of the amplicons of the first set.

C41. The method of any one of embodiments C1 to C40, wherein the hybridization conditions comprise incubating the captured nucleic acid at a temperature between about 25° C. and about 70° C.

C42. The method of embodiment C41, wherein the incubating is at a temperature between about 35° C. and about 60° C.

C43. The method of any one of embodiments C41 to C42, wherein the incubating is for an amount of time between about 1 hour and about 24 hours.

C44. The method of any one of embodiments C41 to C43, wherein the incubating is for an amount of time between about 12 hours and about 20 hours.

C45. The method of any one of embodiments C1 to C44, wherein the hybridizing in (d) comprises contacting the mixture with a hybridization buffer.

C46. The method of any one of embodiments C1 to C45, wherein the hybridizing in (d) comprises the sequential steps of (i) contacting the mixture with a hybridization buffer, (ii) denaturing and (iii) hybridizing.

C47. The method of any one of embodiments C1 to C46, wherein the method does not comprise a drying step.

C48. The method of any one of embodiments C1 to C47, wherein the hybridization conditions do not include a polymerase.

C49. The method of any one of embodiments C1 to C48, wherein the analyzing comprising providing sequence reads.

C50. The method of embodiment C49, wherein the sequence reads are obtained by a method comprising massive parallel sequencing.

C51. The method of embodiment C49, wherein the sequence reads are obtained by a method comprising pair-end sequencing.

C52. The method of any one of embodiments C1 to C51, wherein the first non-native nucleic acid comprises the one or more distinguishable identifiers.

C53. The method of any one of embodiments C1 to C52, wherein the second non-native nucleic acid comprises the one or more distinguishable identifiers.

C54. The method of any one of embodiments C1 to C53, wherein the one or more distinguishable identifiers comprise a nucleic acid barcode.

C55. The method of any one of embodiments C1 to C54, wherein the one or more blocking nucleic acids comprise locked nucleic acids.

C56. The method of any one of embodiments C1 to C55, wherein the one or more blocking nucleic acids comprise bridged nucleic acids.

C57. The method of any one of embodiments C1 to C56, wherein the method does not comprise a denaturation step prior to (c).

C58. The method of any one of embodiments C1 to C57, wherein the method does not comprise a denaturation step prior to (d).

C59. The method of any one of embodiments C1 to C58, wherein the method does not comprise heating to a temperature above 80° C. prior to (d).

C60. The method of any one of embodiments C1 to C59, wherein the method does not comprise heating to a temperature above 90° C. prior to (d).

C61. The method of any one of embodiments C1 to C60, wherein the captured nucleic acid comprises a subset of the nucleic acids of the library.

C62. The method of any one of embodiments C1 to C61, wherein the one or more samples comprise 10 or more samples.

C63. The method of any one of embodiments C1 to C62, wherein the one or more distinguishable identifiers consist of 10 or more distinguishable identifiers.

C64. The method of any one of embodiments C1 to C63, wherein the first nucleic acid and the second nucleic acid comprise synthetic nucleic acids.

C65. The method of any one of embodiments C1 to C64, wherein the library insert comprises a portion of genomic nucleic acid.

C66. The method of any one of embodiments C1 to C65, wherein the purifying in (c) does not comprise addition of a second member of a binding pair configured to bind to the first member of the binding pair.

C67. The method of embodiment C1, wherein the purifying in (c) comprises a method of non-specifically binding nucleic acids to a substrate.

C68. The method of any one of embodiments C1 to C67, wherein the purifying in (c) comprises use of an anion exchange resin.

C69. The method of any one of embodiments C1 to C68, wherein the capturing in (e) comprises addition of a second member of a binding pair configured to bind to the first member of the binding pair.

C70. The method of any one of embodiments C1 to C69, wherein prior to (e), the mixture is not immobilized on a substrate of a flow cell or an array.

D1. A method of analyzing a genomic DNA library comprising:
  a) obtaining a genomic DNA library comprising a first set of single-stranded amplicons, wherein each amplicon comprises a first non-native nucleic acid and a second non-native nucleic acid, one or two nucleic acid barcodes, and a library insert obtained from a genome of one of ten or more human subjects, wherein the library insert is located between the first and the second non-native nucleic acids, and wherein the first set of amplicons comprises a plurality of the library inserts from the ten or more human subjects;
  b) preparing a mixture comprising contacting the first set of amplicons with one to four blocking nucleic acids, C0t-1 DNA and capture nucleic acids, wherein
    (i) the one to four blocking nucleic acids are configured to specifically hybridize to the first and/or second non-native nucleic acids,
    (ii) the one to four blocking nucleic acids comprise locked nucleic acids and comprise a length of 10 to 30 nucleotides,
    (iii) the capture nucleic acids comprise biotin, and
    (iv) the capture nucleic acids are configured to specifically hybridize to a subset of the plurality of library inserts;
  c) contacting the mixture with magnetic beads comprising a non-specific nucleic acid binding substrate thereby providing purified nucleic acid, wherein the purified nucleic acid comprises the first set of amplicons, the one or four blocking nucleic acids, the C0t-1 DNA and the capture nucleic acids;
  d) hybridizing the purified nucleic acid wherein the hybridizing comprises the sequential steps of (i) contacting the mixture with a hybridization buffer, (ii) heating the purified nucleic acids to at least 95° C. for about 10 minutes and (iii) hybridizing the purified nucleic acids by incubating at about 40° C. to 50° C. for 12 to 20 hours;
  e) capturing the capture nucleic acids, wherein the capturing comprises contacting the purified nucleic acids with avidin coated magnetic beads configured to specifically bind to the capture nucleic acids and immobilizing the captured nucleic acids using a magnet, thereby providing captured nucleic acid;
  f) contacting the captured nucleic acid with a set of primers under amplification condition, thereby providing a second set of amplicons; and
  g) obtaining sequence reads from the second set of amplicons by a method comprising pair-end sequencing, wherein the method does not comprise a drying step.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology. Certain embodiments of the technology are set forth in the claim(s) that follow(s).

What is claimed is:

1. A composition for use in massive parallel nucleic acid sequencing comprising:
  a) a library of nucleic acids comprising a plurality of library inserts wherein each nucleic acid of the library comprises (i) at least one library insert obtained from one of four or more samples, (ii) a first non-native nucleic acid, and (iii) a second non-native nucleic acid, wherein the first non-native nucleic acid and the second non-native nucleic acid are located on opposing sides of the at least one library insert, and the first non-native nucleic acid comprises a first distinguishable nucleic acid barcode and the second non-native nucleic acid comprises a second distinguishable nucleic acid barcode, wherein the first and second distinguishable nucleic acid barcodes are unique to the one of the four or more samples; and
  b) four universal blocking (U-block) nucleic acids, wherein (i) a first U-block nucleic acid and a second U-block nucleic acid are configured to hybridize to the first non-native nucleic acid on opposing sides of the first distinguishable nucleic acid barcode, (ii) a third U-block nucleic acid and a fourth U-block nucleic acid are configured to hybridize to the second non-native nucleic acid on opposing sides of the second distinguishable nucleic acid barcode, and (iii) each of the U-block nucleic acids does not substantially hybridize to a portion of the first or second distinguishable nucleic acid barcode.

2. The composition of claim 1, wherein the library of nucleic acids comprises at least eight distinguishable nucleic acid barcodes, and optionally, wherein each of the at least eight distinguishable nucleic acid barcodes is present on a different nucleic acid of the library.

3. The composition of claim 1, wherein the first and second U-block nucleic acids are substantially complementary to a portion of the first non-native nucleic acid, and the third and fourth U-block nucleic acids are substantially complementary to a portion of the second non-native nucleic acid.

4. The composition of claim 1, comprising no more than four U-block nucleic acids.

5. The composition of claim 1, comprising one or more capture nucleic acids, wherein,
   (i) the capture nucleic acids comprise a member of a binding pair; and
   (ii) each of the capture nucleic acids is configured to specifically hybridize to a subset of nucleic acids of the library.

6. The composition of claim 1, wherein the library of nucleic acids comprises ten or more distinguishable nucleic acid barcodes.

7. The composition of claim 1, wherein the first and second non-native nucleic acids comprise adapter nucleic acids.

8. The composition of claim 1, wherein each of the four U-block nucleic acids comprises a length of 10 to 40 nucleotides.

9. The composition of claim 1, wherein each of the four U-block nucleic acids comprises locked nucleic acids.

10. The composition of claim 1, wherein each of the four U-block nucleic acids comprises bridged nucleic acids.

11. The composition of claim 1, wherein each of the four U-block nucleic acids has a melting temperature of at least 65° C.

12. The composition of claim 1, wherein the four U-block nucleic acids do not substantially hybridize to a distinguishable nucleic acid barcode.

13. The composition of claim 1, wherein the four U-block nucleic acids comprise a chain terminator.

14. A method of analyzing a nucleic acid library comprising:
   a) obtaining a library of nucleic acids comprising a plurality of library inserts wherein each nucleic acid of the library comprises (i) at least one library insert obtained from one of four or more samples, (ii) a first non-native nucleic acid, and (iii) a second non-native nucleic acid, wherein the first non-native nucleic acid and the second non-native nucleic acid are located on opposing sides of the at least one library insert, and the first non-native nucleic acid comprises a first distinguishable nucleic acid barcode and the second non-native nucleic acid comprises a second distinguishable nucleic acid barcode, wherein the first and second distinguishable nucleic acid barcodes are unique to the one of the four or more samples;
   b) contacting the library of nucleic acids with four universal blocking (U-block) nucleic acids, wherein (i) a first U-block nucleic acid and a second U-block nucleic acid are configured to hybridize to the first non-native nucleic acid on opposing sides of the first distinguishable nucleic acid barcode, (ii) a third U-block nucleic acid and a fourth U-block nucleic acid are configured to hybridize to the second non-native nucleic acid on opposing sides of the second distinguishable nucleic acid barcode, and (iii) each of the U-block nucleic acids does not substantially hybridize to a portion of the first or second distinguishable nucleic acid barcode;
   c) contacting the library of nucleic acids with one or more capture nucleic acids, each comprising a first member of a binding pair, wherein the one or more capture nucleic acids are configured to specifically hybridize to a subset of the nucleic acids of the library;
   d) capturing the capture nucleic acids, thereby providing captured nucleic acids comprising the subset of nucleic acids of the library;
   e) contacting the captured nucleic acids with a set of primers under amplification condition, thereby providing amplicons; and
   f) analyzing the amplicons.

15. The method of claim 14, wherein the library of nucleic acids comprises ten or more distinguishable nucleic acid barcodes.

16. The method of claim 14, wherein each of the four U-block nucleic acids comprises a length of 10 to 40 nucleotides.

17. The method of claim 14, wherein each of the four U-block nucleic acids comprises locked nucleic acids.

18. The method of claim 14, wherein each of the four U-block nucleic acids comprises bridged nucleic acids.

19. The method of claim 14, wherein each of the four U-block nucleic acids has a melting temperature of at least 65° C.

* * * * *